United States Patent [19]

Boden

[11] 4,391,999
[45] Jul. 5, 1983

[54] 3,4,5,6,6-PENTAMETHYL HEXANOL-2 AND ALKYL HOMOLOGUES THEREOF; PROCESS FOR PREPARING SAME AND ORGANOLEPTIC USES THEREOF

[75] Inventor: Richard M. Boden, Ocean, N.J.

[73] Assignee: International Flavors & Fragrances Inc., New York, N.Y.

[21] Appl. No.: 399,066

[22] Filed: Jul. 16, 1982

Related U.S. Application Data

[60] Continuation-in-part of Ser. No. 354,389, Mar. 2, 1982, which is a division of Ser. No. 252,334, Apr. 9, 1981, Pat. No. 4,336,164, which is a continuation-in-part of Ser. No. 212,887, Dec. 4, 1980, Pat. No. 4,318,934.

[51] Int. Cl.$^3$ ............ C07C 31/125; A24B 3/12; C11D 3/50
[52] U.S. Cl. ............ 568/840; 131/276; 252/174.11; 252/522 R; 568/881; 568/903
[58] Field of Search ............ 508/903, 881, 840

[56] References Cited

U.S. PATENT DOCUMENTS 2,810,763 10/1957 Hadley et al. .................. 568/881
3,959,396 5/1976 Ochsner et al. ................. 568/903

Primary Examiner—J. E. Evans
Attorney, Agent, or Firm—Arthur L. Liberman

[57] ABSTRACT

Described is the novel compound genus defined according to the structure:

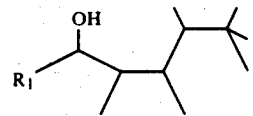

wherein $R_1$ is selected from the group consisting of $C_1$–$C_3$ alkyl useful in augmenting or enhancing the aroma or taste of consumable materials including perfumes, colognes, perfumed articles (including a solid or liquid anionic, cationic, nonionic or zwitterionic detergents) smoking tobacco and smoking tobacco articles.

6 Claims, 27 Drawing Figures

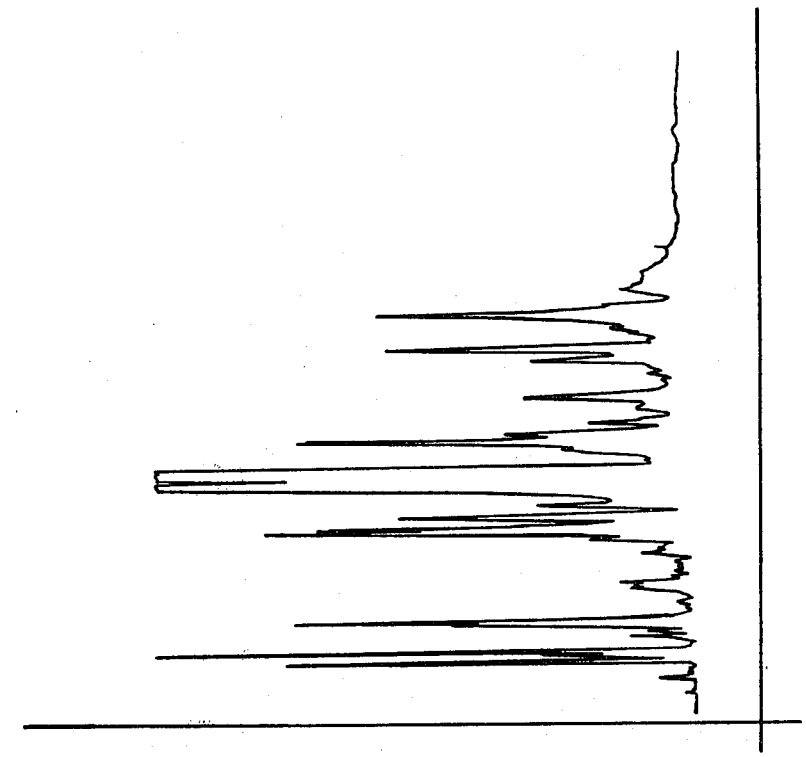
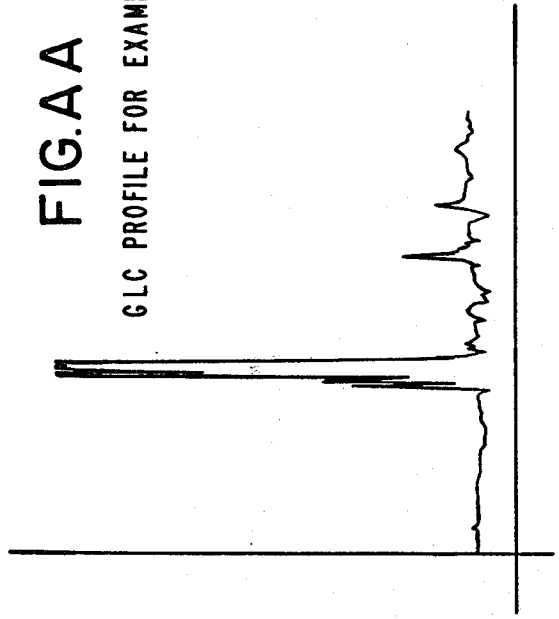
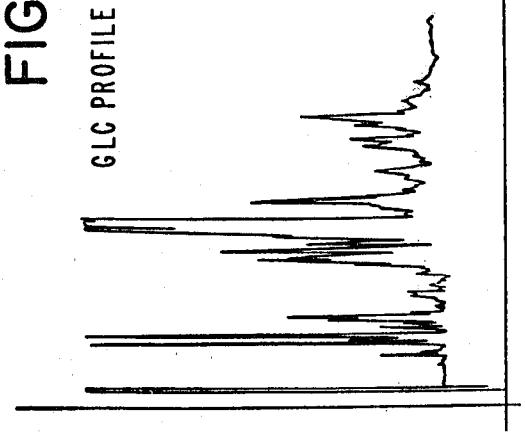

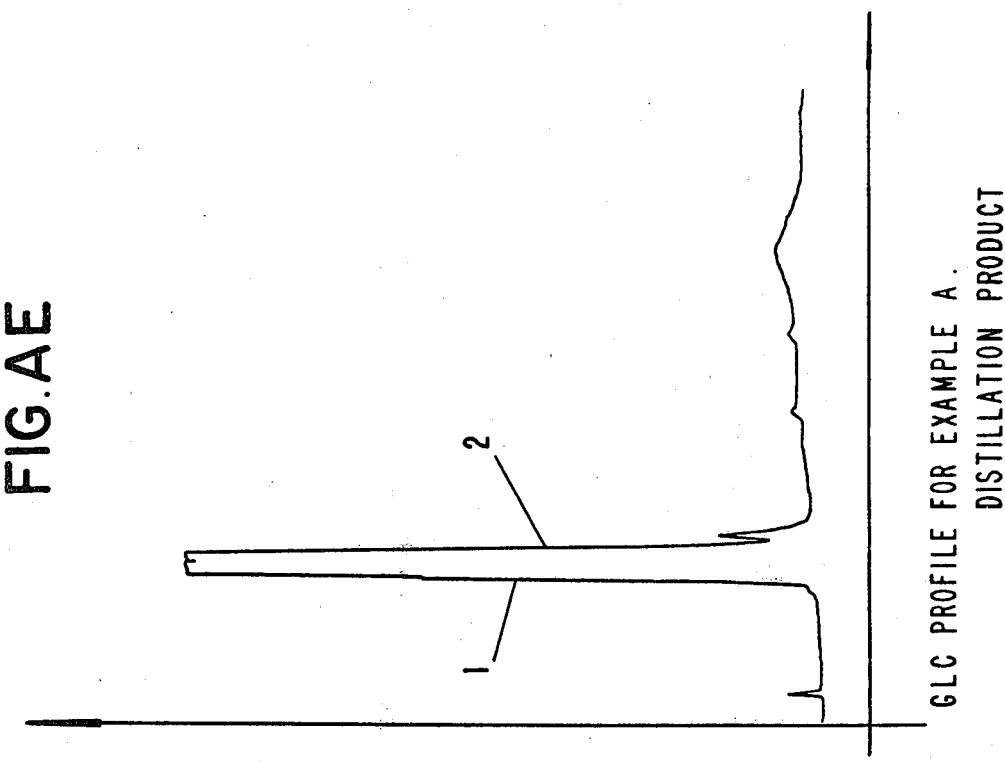
FIG.AE
GLC PROFILE FOR EXAMPLE A.
DISTILLATION PRODUCT
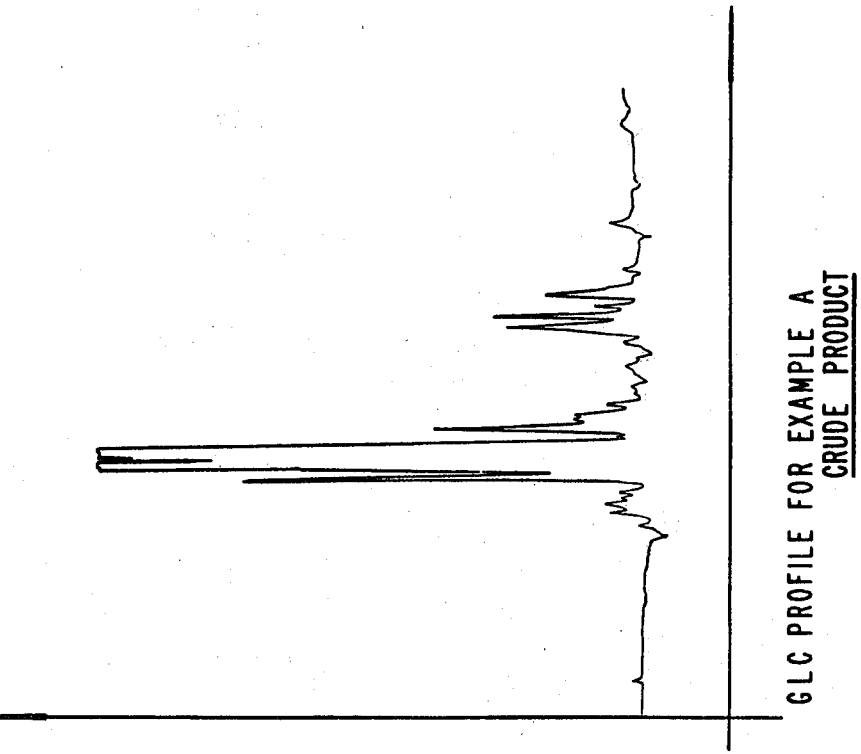
FIG.AD
GLC PROFILE FOR EXAMPLE A
CRUDE PRODUCT

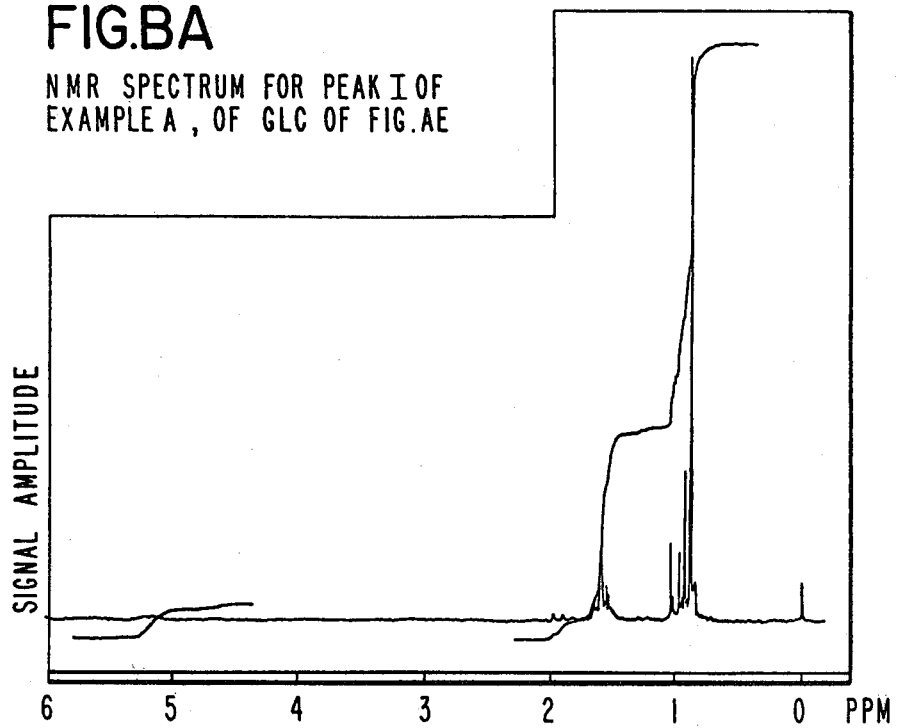
FIG.BA
NMR SPECTRUM FOR PEAK I OF EXAMPLE A, OF GLC OF FIG.AE
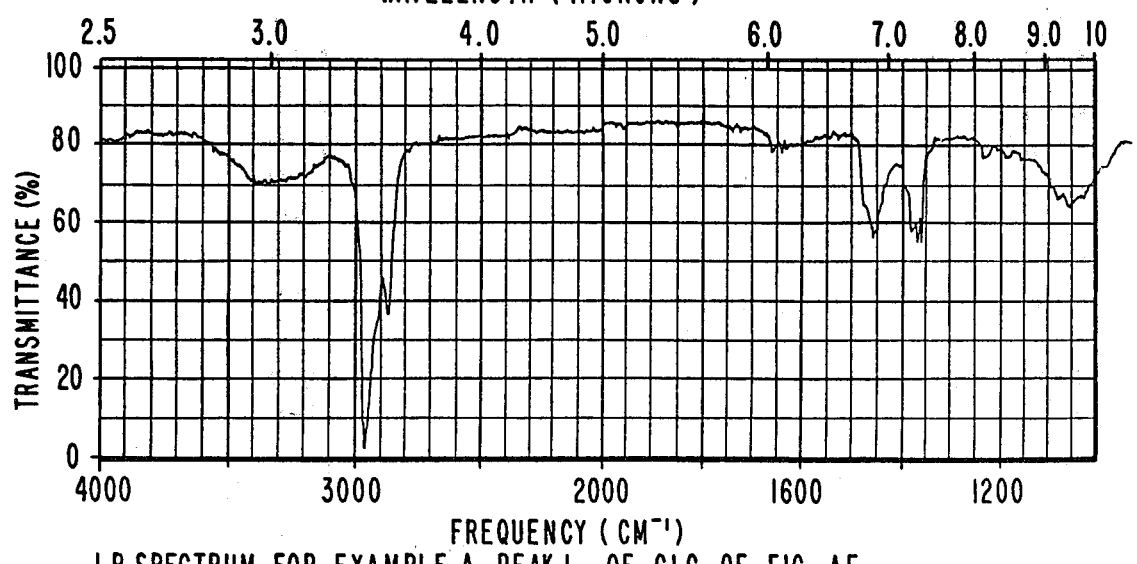
IR SPECTRUM FOR EXAMPLE A, PEAK I, OF GLC OF FIG. AE.
FIG.BB

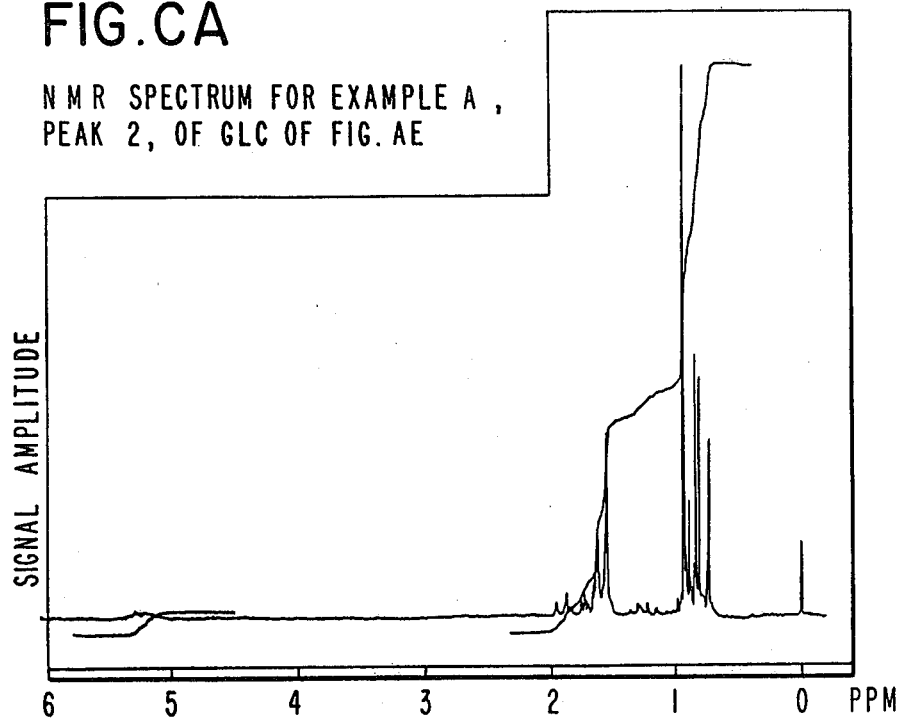
FIG.CA
NMR SPECTRUM FOR EXAMPLE A, PEAK 2, OF GLC OF FIG. AE
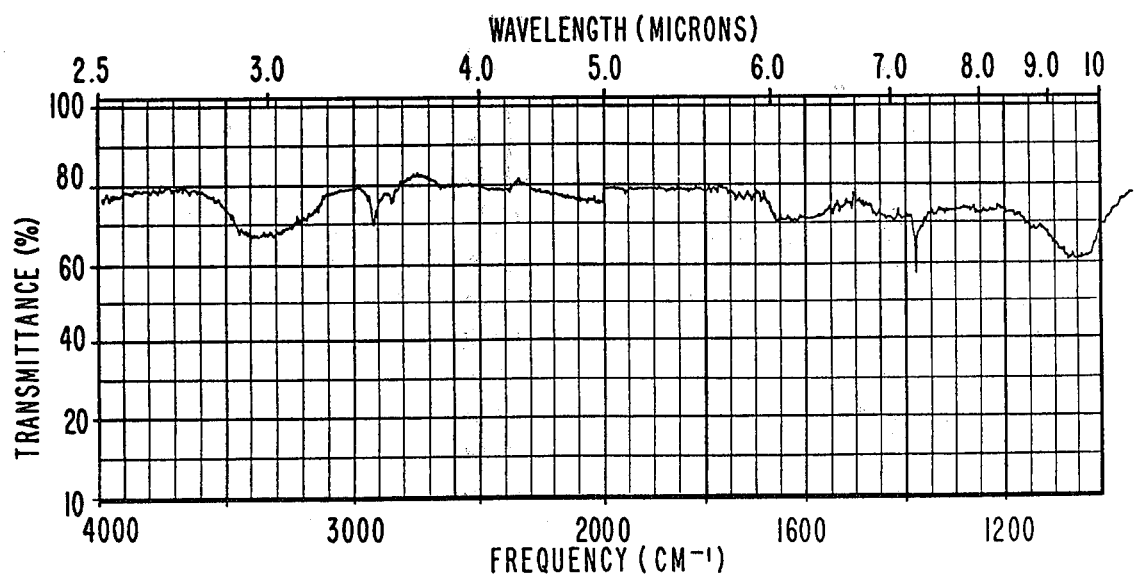
IR SPECTRUM FOR EXAMPLE I, PEAK 2 OF GLC OF FIG.AE
FIG.CB

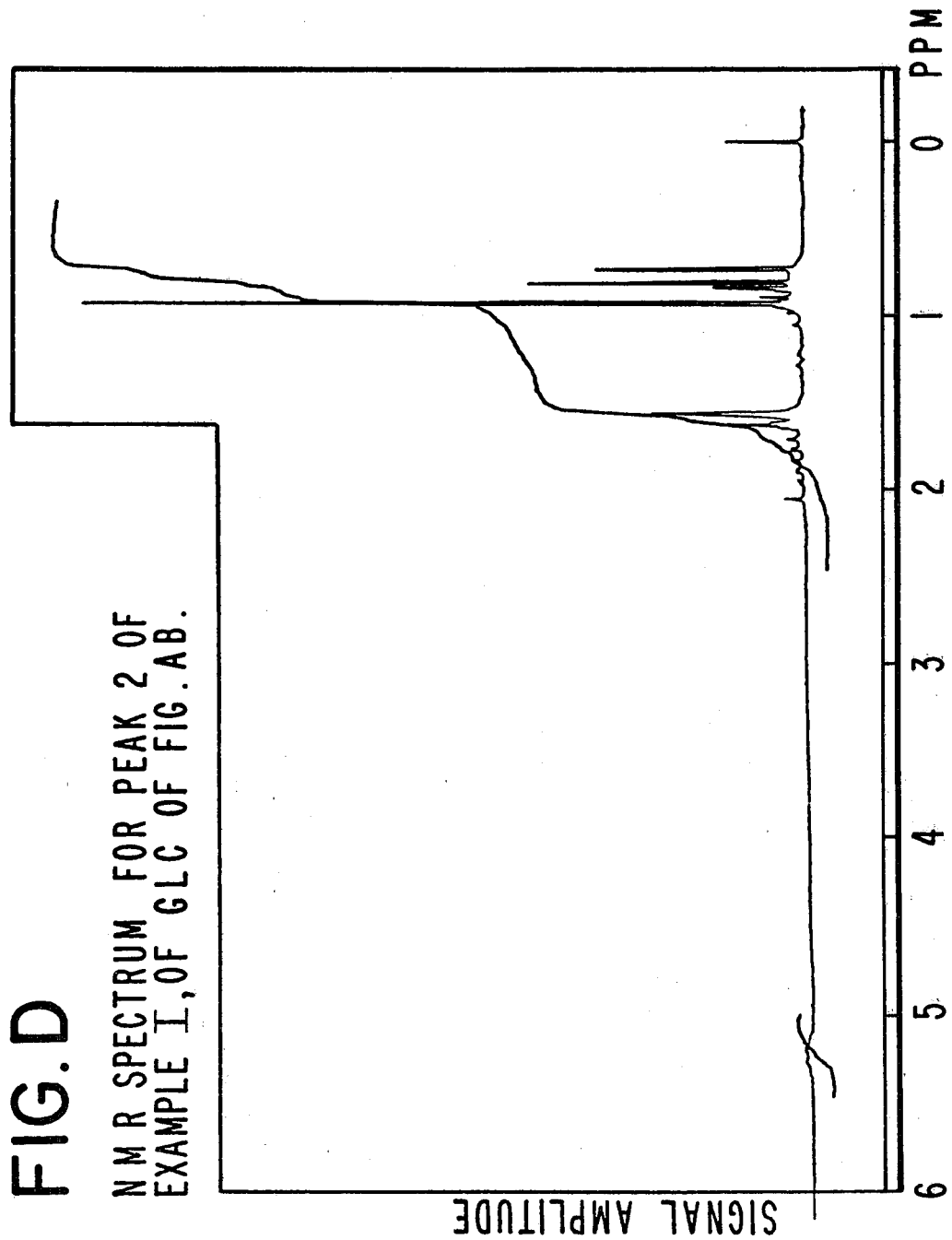
FIG. D  NMR SPECTRUM FOR PEAK 2 OF EXAMPLE I, OF GLC OF FIG. AB.

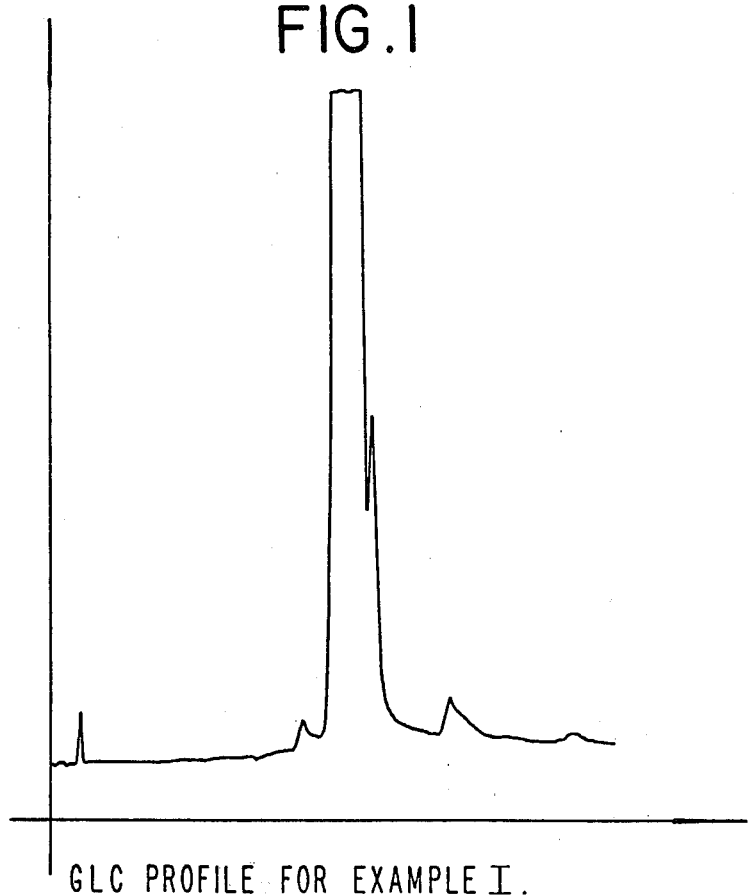
GLC PROFILE FOR EXAMPLE I.
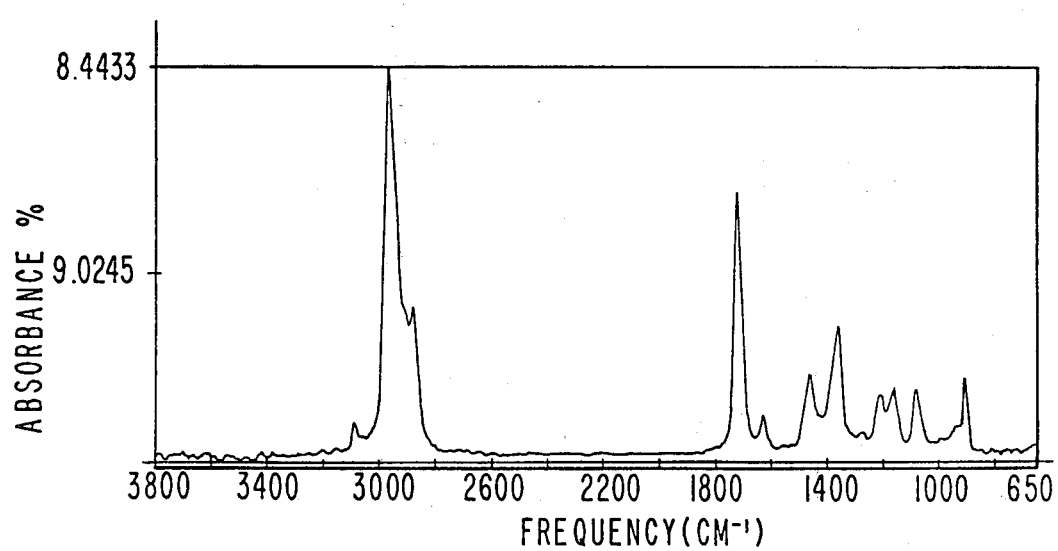
IR SPECTRUM FOR PEAK 3 OF EXAMPLE I.

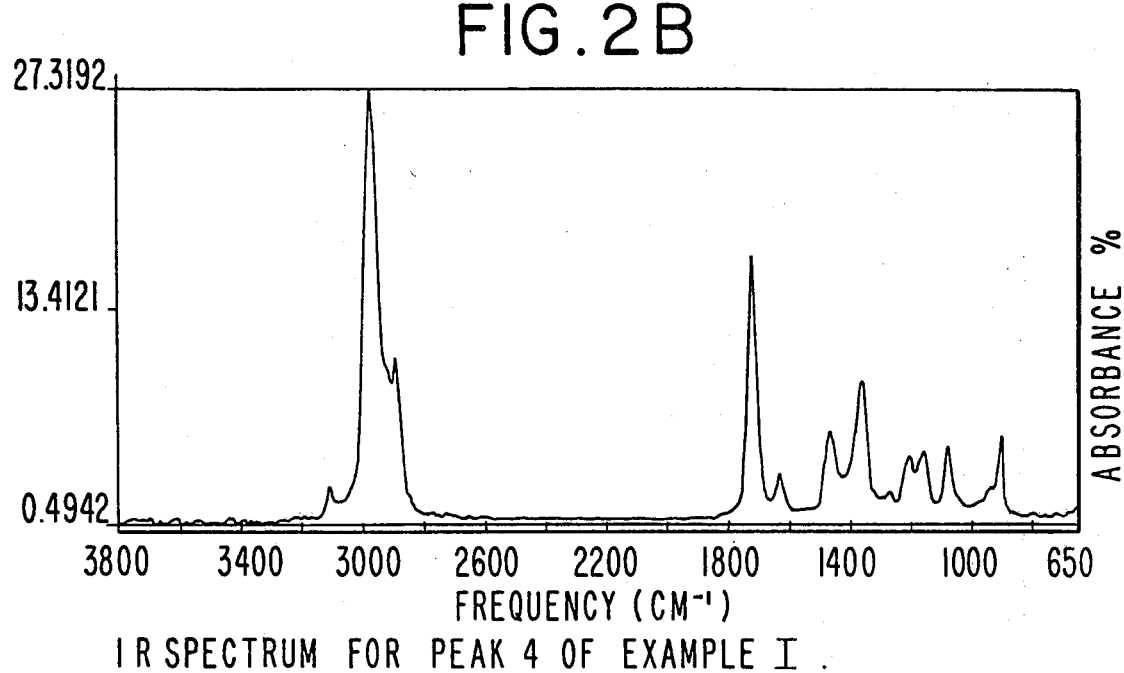
IR SPECTRUM FOR PEAK 4 OF EXAMPLE I.
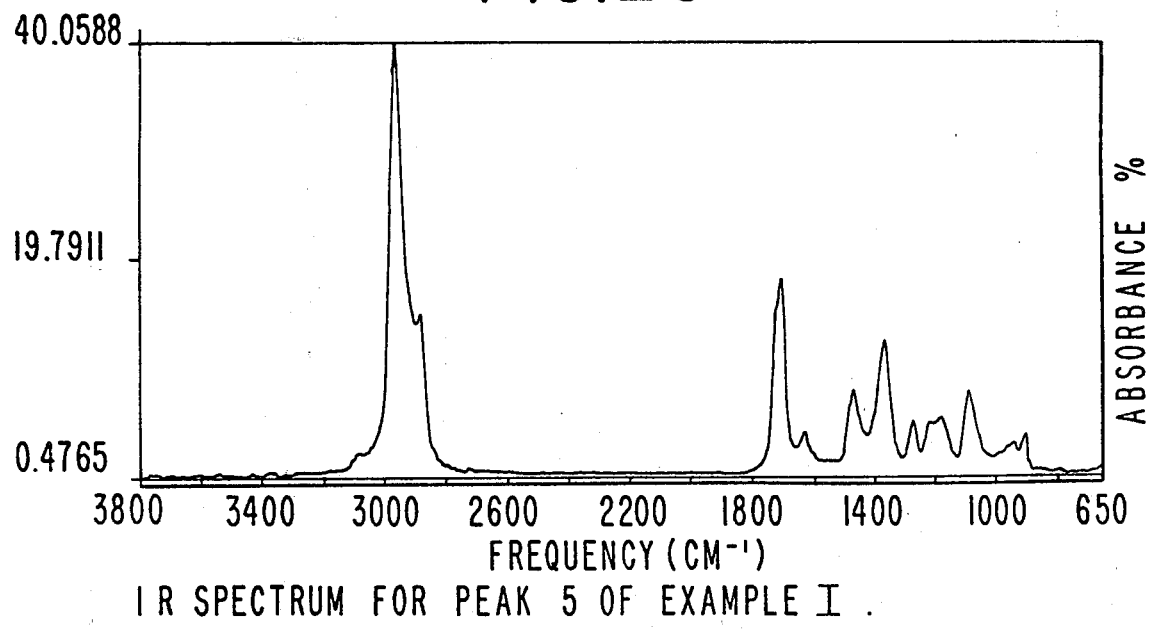
IR SPECTRUM FOR PEAK 5 OF EXAMPLE I.

IR SPECTRUM FOR PEAK 6 OF EXAMPLE I.

IR SPECTRUM FOR PEAK 7 OF EXAMPLE I.

IR SPECTRUM FOR PEAK 8 OF EXAMPLE I.

IR SPECTRUM FOR PEAK 9 OF EXAMPLE I.

IR SPECTRUM FOR PEAK 10 OF EXAMPLE I.

NMR SPECTRUM FOR EXAMPLE I.

NMR SPECTRUM FOR EXAMPLE I.

NMR SPECTRUM FOR EXAMPLE I

GLC PROFILE FOR BULKED FRACTIONS 12-15 OF EXAMPLE III.

GLC PROFILE FOR EXAMPLE II. CRUDE

GLC PROFILE FOR BULKED FRACTIONS 4-7 OF EXAMPLE II.

IR SPECTRUM FOR BULKED FRACTIONS 12-15 OF EXAMPLE II.

NMR SPECTRUM FOR BULKED FRACTIONS 12-15 OF EXAMPLE III.

3,4,5,6,6-PENTAMETHYL HEXANOL-2 AND ALKYL HOMOLOGUES THEREOF; PROCESS FOR PREPARING SAME AND ORGANOLEPTIC USES THEREOF

This application is a continuation-in-part of application for U.S. Letters Patent, Ser. No. 354,389 filed on Mar. 2, 1982 which, in turn, is a division of application for U.S. Letters Patent, Ser. No. 252,334 filed on Apr. 9, 1981 (now U.S. Pat. No. 4,336,164 issued on June 22, 1982) which, in turn, is a continuation-in-part of application for U.S. Letters Patent, Ser. No. 212,887 filed on Dec. 4, 1980, now U.S. Pat. No. 4,318,934 issued on Mar. 9, 1982.

BACKGROUND OF THE INVENTION

Materials which can provide woody (sawdust), mossy, and vetiver aroma profiles with amber-like undertones particularly those materials which are relatively inexpensive and are highly sought after in the art of perfumery. Many of the natural materials which provide such fragrance profiles and contribute desired nuances to perfumery compositions and perfumed article substances are high in cost, vary in quality from one batch to another and/or are generally subject to the usual variations of natural products.

There is, accordingly, a continuing effort to find synthetic materials which will replace the essential fragrance notes produced by natural essential oils or compositions thereof. Unfortunately, many of these synthetic materials either have the desired nuances only to a relatively small degree or else contribute undesirable or unwanted odor to the composition. The search for materials which can provide a more refined woody (sawdust), mossy, vetiver-like aroma with amber undertones has been difficult and relatively costly in the areas of both natural products and synthetic products.

Materials which can provide woody, vetiver, musty, earthy and oriental aroma and taste profiles both prior to and on smoking in the mainstream and the sidestream of smoking tobacco articles are desirable for augmenting or enhancing the aroma and taste of smoking tobacco and smoking tobacco articles, e.g., cigarettes and cigars.

Even more desirable is a product that can serve to substitute for difficult-to-obtain natural perfumery oils and expensive synthetic ingredients of perfume compositions and, at the same time, substitute for expensive flavoring ingredients in smoking tobacco and in smoking tobacco articles.

Perfumery materials which are inexpensive such as dihydro linalool (3,7-dimethyl-6-octen-3-ol) and dihydro myrcenol (3-methylene-7-methyloctanol-7) do not provide the vetiver-like fragrance profiles that are provided by the more expensive, more complex molecules such as vetivone.

Dihydro linalool according to "Perfume and Flavor Chemicals (Aroma Chemicals)" by Steffen Arctander (1969) having the structure:

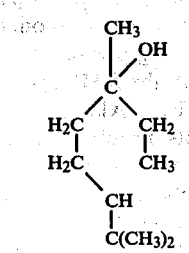

at Monograph 960 is indicated to have a fresh, floral, citrusy aroma which is less woody than linalool and more powerful and more lime-like than tetrahydro linalool. On the other hand, dihydro myrcenol having the structure:

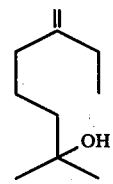

(at number 964 of Arctander) is described as being powerful, fresh lime-like overall citrusy, floral and sweet with little or no terpenic undertones. Dihydro myrcenyl acetate described at Monograph 965 of Arctander having the structure:

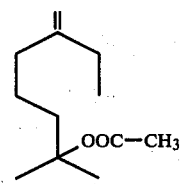

is described as sweet, spicy, herbaceous, fresh and somewhat fruity with a bergamot-like character but poor tenacity.

The chemicals described in the prior art such as dihydro myrcenyl acetate, dihydro myrcenol or dihydro linalool have aroma profiles or chemical structures which are not even remotely similar to the compounds of our invention.

BRIEF DESCRIPTION OF THE DRAWINGS

FIG. AA represents the GLC profile for the reaction product of Example A using a 70% sulfuric acid catalyst at 35° C.

FIG. AB represents the GLC profile for the reaction product of Example A using an Amberlyst ® 15 acidic ion exchange resin catalyst at a temperature of 150° C.

FIG. AC represents the GLC profile for the reaction product of Example A, using an Amberlyst ® 15 catalyst at 100° C.

FIG. AD represents the GLC profile for the reaction product of Example A, using a sulfuric acid catalyst and an alpha-methylstyrene diluent at 35° C. according to the conditions of United Kingdom patent specification No. 796,130 (crude reaction product).

FIG. AE represents the GLC profile for the reaction product of Example A, using a sulfuric acid catalyst, at 35° C. and an alpha-methyl styrene diluent according to the conditions of United Kingdom patent specification No. 796,130 (distilled reaction product) (boiling range 36°-38° C. at 4-5 mmHg. pressure).

FIG. BA represents the NMR spectrum for Peak 1 of the GLC profile of FIG. AE.

FIG. BB represents the infra-red spectrum for Peak 1 of the GLC profile of FIG. AE.

FIG. CA represents the NMR spectrum for Peak 2 of the GLC profile of FIG. AE.

FIG. CB represents the infra-red spectrum for Peak 2 of the GLC profile of FIG. AE.

FIG. D represents the NMR spectrum for Peak 2 of the GLC profile of FIG. AB.

FIG. 1 sets forth the GLC profile for the reaction product of Example I, containing compounds defined according to the structure:

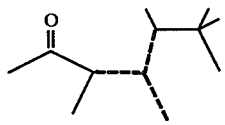

wherein in each molecule of the mixture, one of the dashed lines is a carbon-carbon double bond and the other of the dashed lines are carbon-carbon single bonds.

FIG. 2A represents the infra-red spectrum for Peak 3 of the GLC profile of FIG. 1.

FIG. 2B represents the infra-red spectrum of Peak 4 of the GLC profile of FIG. 1.

FIG. 2C represents the infra-red spectrum for Peak 5 of the GLC profile of FIG. 1.

Figure 2D:
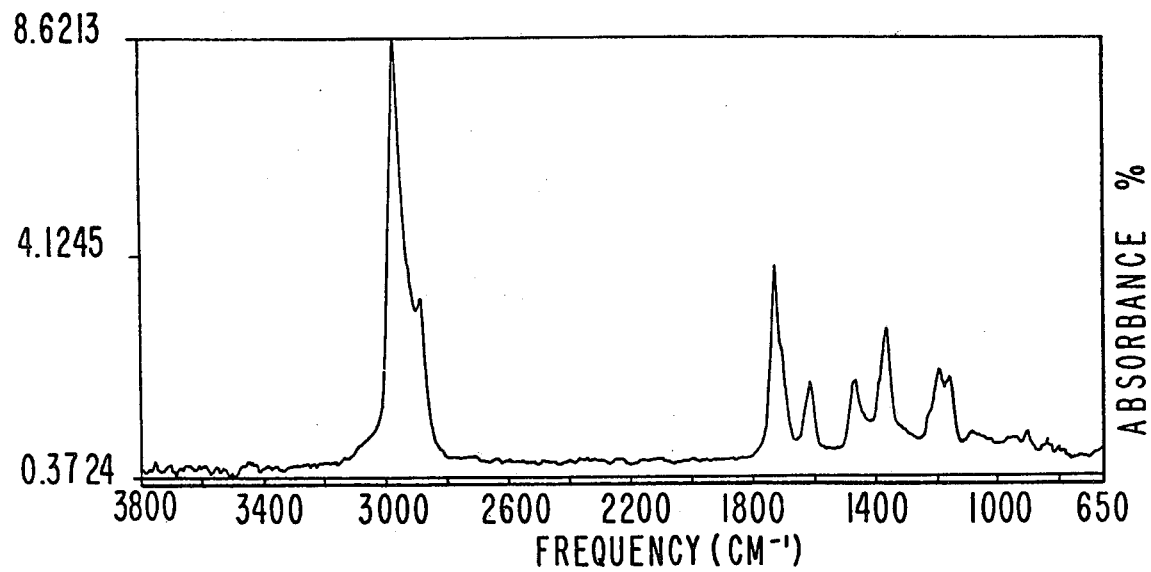

FIG. 2D represents the infra-red spectrum for Peak 6 of the GLC profile of FIG. 1.

Figure 2E:
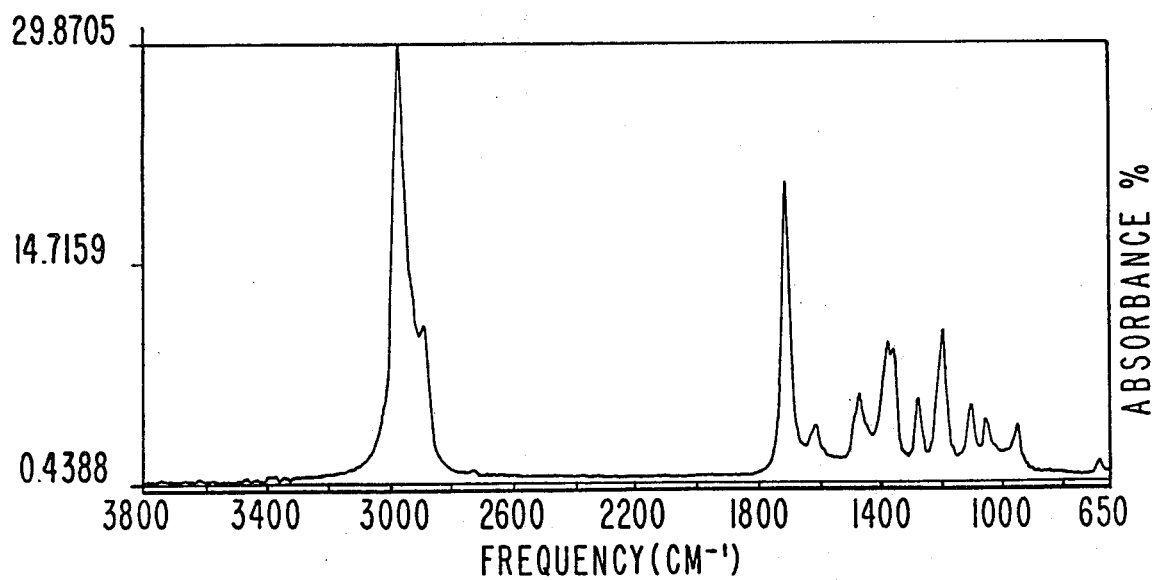

FIG. 2E represents the infra-red spectrum for Peak 7 of the GLC profile of FIG. 1.

Figure 2F:
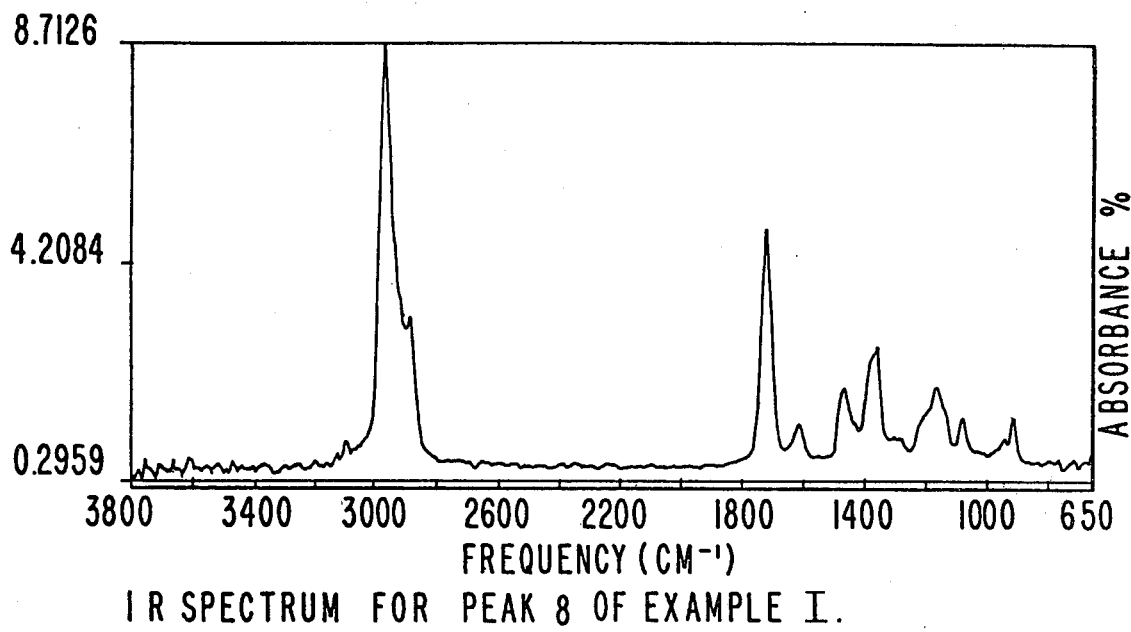

FIG. 2F represents the infra-red spectrum for Peak 8 of the GLC profile of FIG. 1.

Figure 2G:
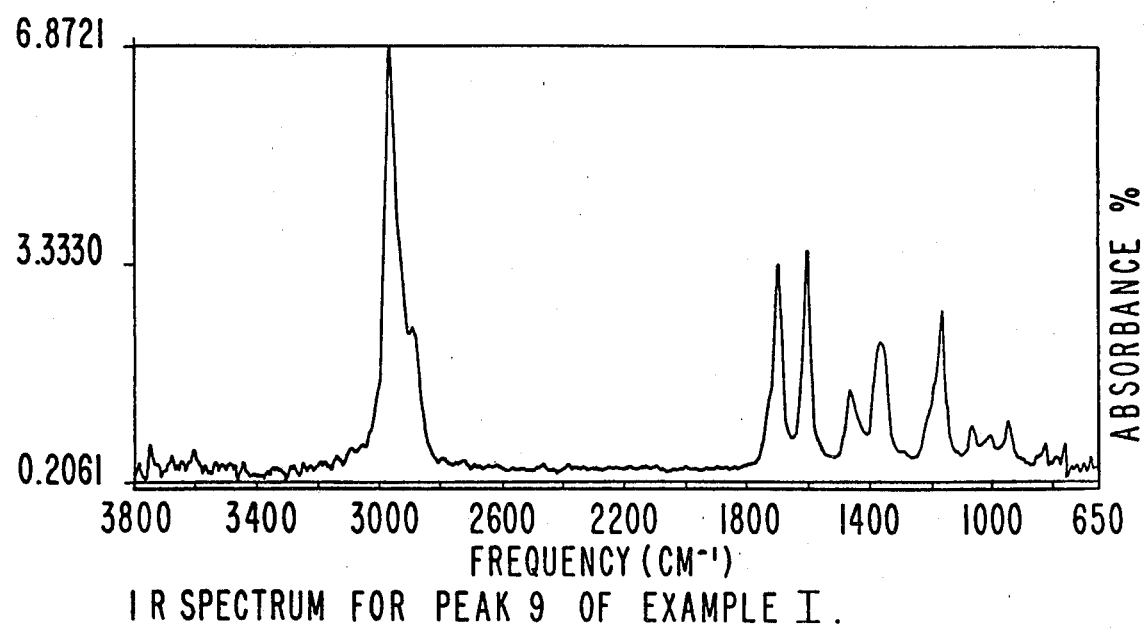

FIG. 2G represents the infra-red spectrum for Peak 9 of the GLC profile of FIG. 1.

Figure 2H:
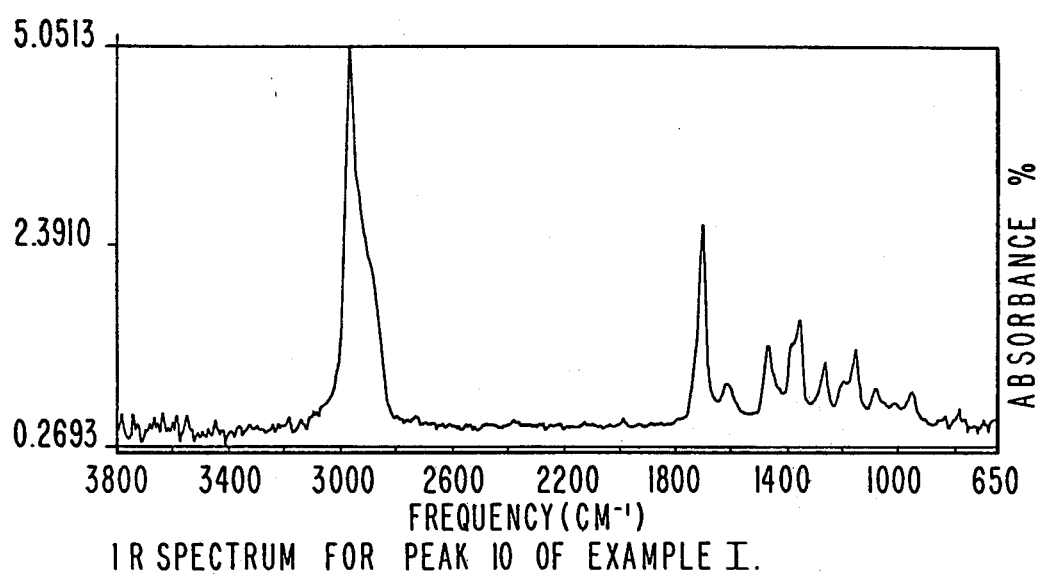

FIG. 2H represents the infra-red spectrum for Peak 10 of the GLC profile of FIG. 1.

Figure 2J:
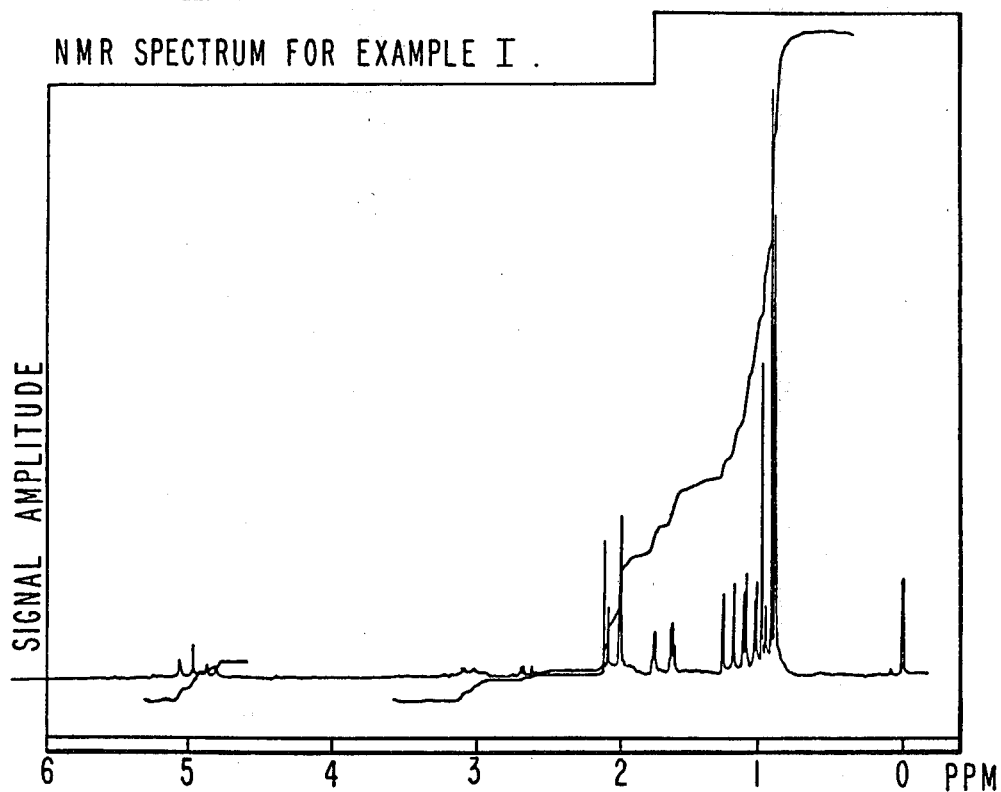

FIG. 2J represents the NMR spectrum for a mixture of compounds having the structures:

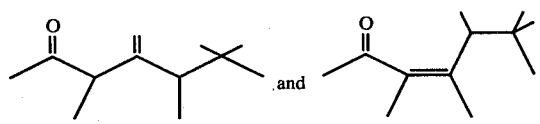

produced according to Example I.

Figure 2K:
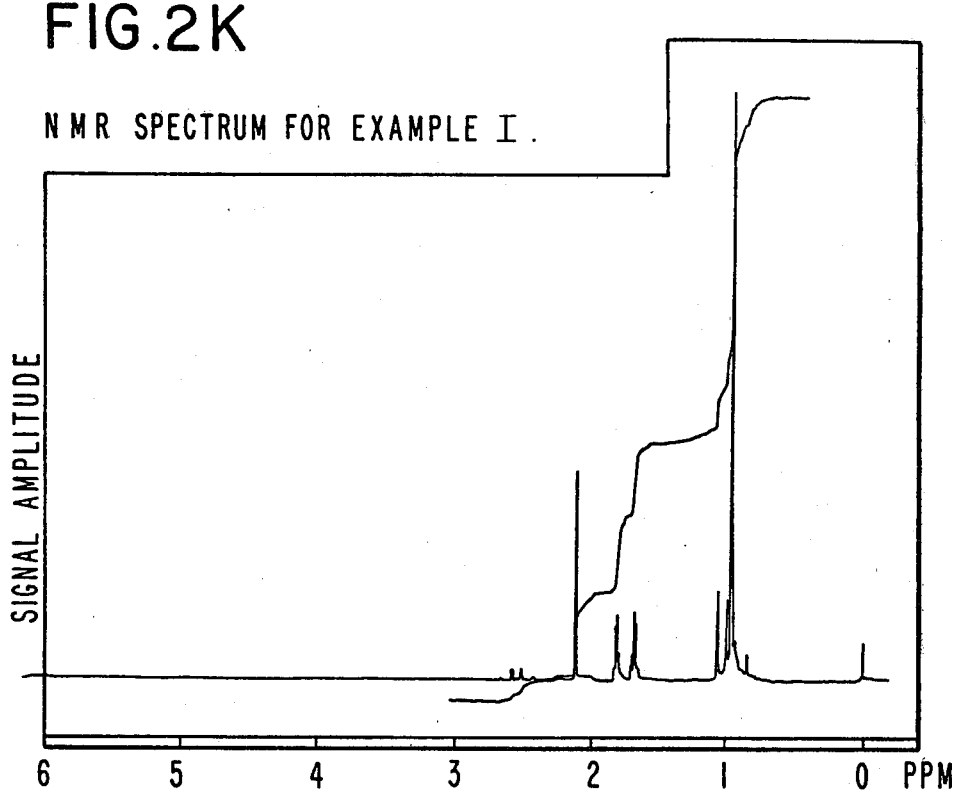

FIG. 2K represents the NMR spectrum for the compound having the structure:

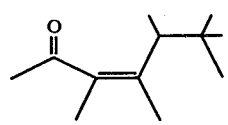

produced according to Example I.

Figure 2L:
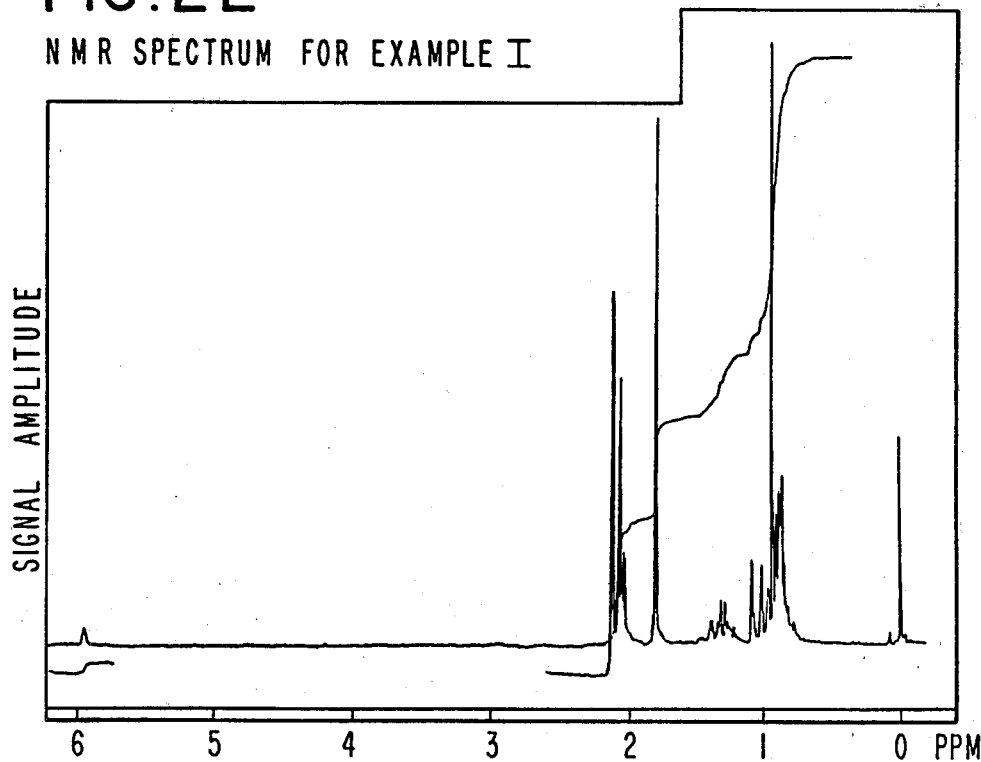

FIG. 2L represents the NMR spectrum for the compound containing the structure:

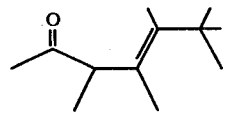

produced according to Example I.

Figure 3:
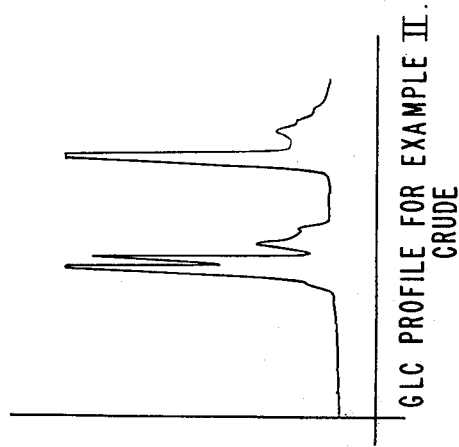

FIG. 3 is the GLC profile for the reaction product of Example II containing a mixture of compounds defined according to the structure:

wherein in each molecule of the mixture, one of the dashed lines is a carbon-carbon double bond and the other of the dashed lines represent carbon-carbon single bond.

Figure 4:
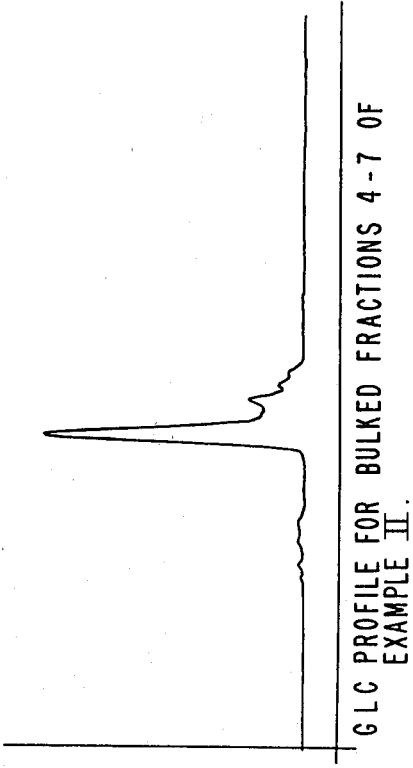

FIG. 4 is the GLC profile for bulked fractions 4-7 of the distillation product of reaction product of Example II containing a compound defined according to the structure:

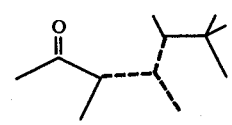

wherein in each molecule of the mixture, one of the dashed lines is a carbon-carbon double bond and the other of the dashed lines are carbon-carbon single bonds.

Figure 5:
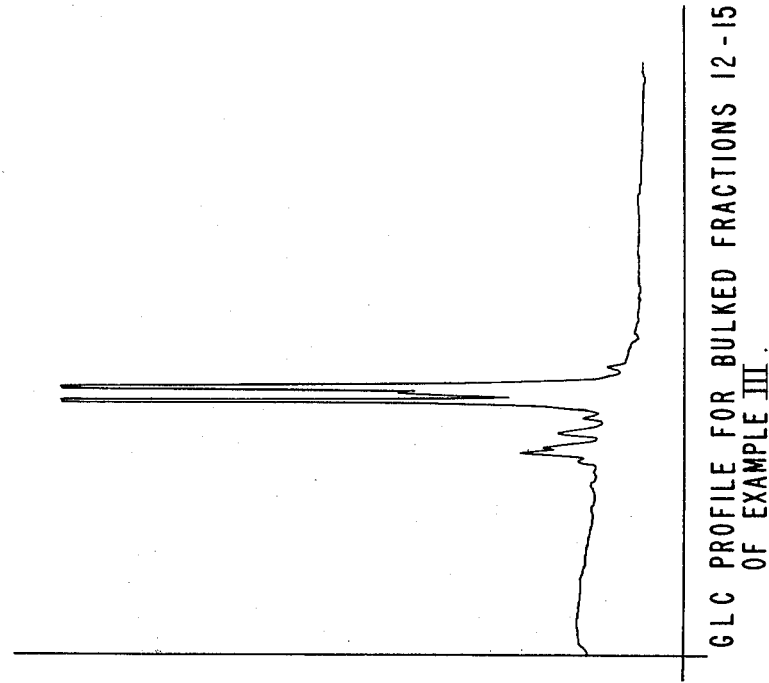

FIG. 5 is the GLC profile for bulked fractions 12-15 of the distillation product of the reaction product of Example III containing the compound having the structure:

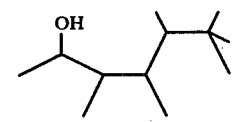

Figure 6:
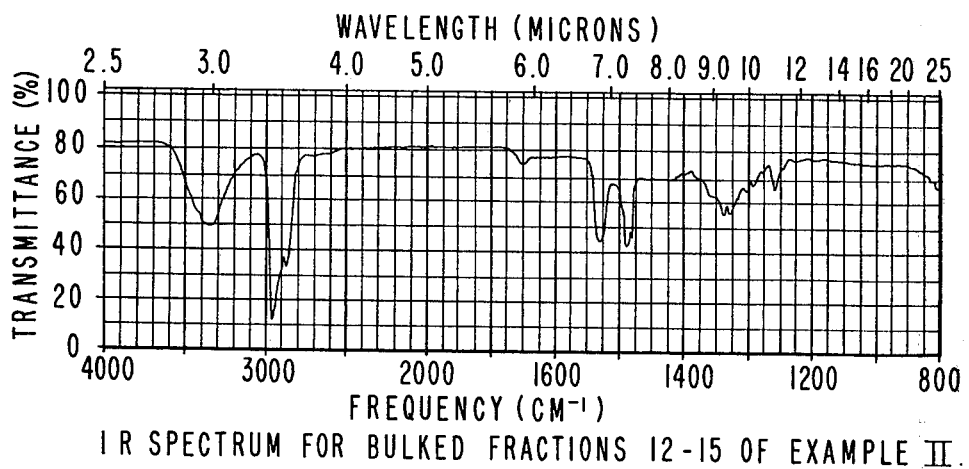

FIG. 6 is the infra-red spectrum for bulked fractions 12-15 of the distillation product of the reaction product of Example III containing the compound defined according to the structure:

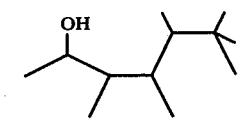

Figure 7:
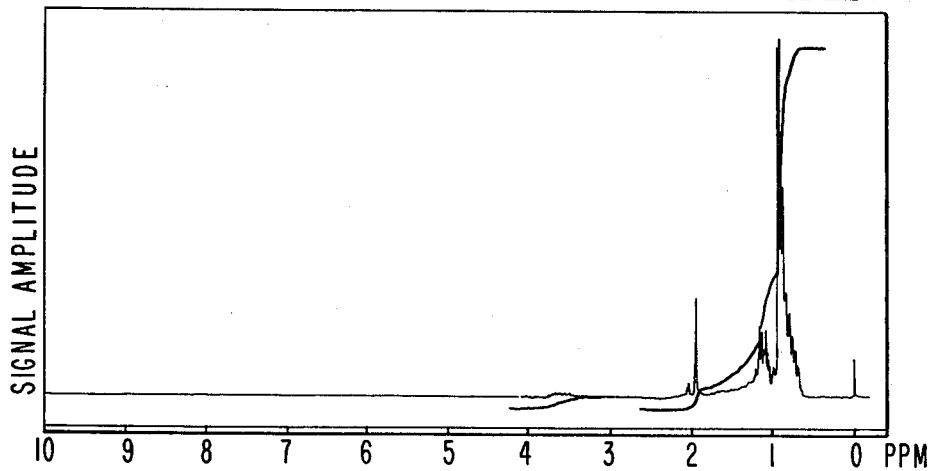

FIG. 7 is the NMR spectrum for bulked fractions 12-15 of the distillation product of the reaction product of Example III containing the compound having the structure:

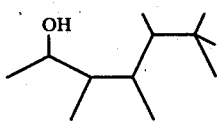

(Solvent: CFCl₃; field strength 100 MHz).

DISCLOSURES INCORPORATED BY REFERENCE HEREIN

The following applications for United States Letters Patent are incorporated by reference herein:

(a) U.S. application for Letters Patent, Ser. No. 160,788 filed on June 19, 1980 now U.S. Pat. No. 4,287,084 issued on Sept. 1, 1981 (entitled: "Use of Mixture of Aliphatic $C_{10}$ Branched Olefins in Augmenting or Enhancing the Aroma of Perfumes and/or Perfumed Articles") setting forth the use of the compounds having the structures:

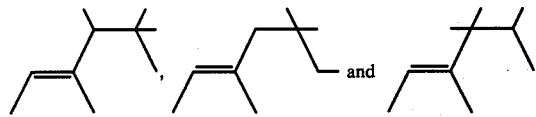

or generically the compounds defined according to the structure:

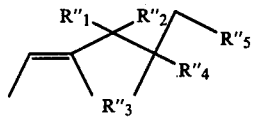

wherein $R_1''$, $R_2''$, $R_3''$, $R_4''$ and $R_5''$ represents hydrogen or methyl with three of $R_1''$, $R_2''$, $R_3''$, $R_4''$ and $R_5''$ representing methyl and the other two of $R_1''$, $R_2''$, $R_3''$, $R_4''$ and $R_5''$ representing hydrogen;

(b) Application for U.S. Letters Patent, Ser. No. 188,576 filed on Sept. 18, 1980 now U.S. Pat. No. 4,303,555 issued on Dec. 1, 1981, a continuation-in-part of Ser. No. 160,788 filed on June 19, 1980; and (c) Application for U.S. Letters Patent, Ser. No. 184,132 filed on Sept. 4, 1980 now U.S. Pat. No. 4,321,255 issued on Mar. 23, 1982 entitled "Branched Ketones, Organoleptic Uses Thereof and Process for Preparing Same" disclosing the reaction:

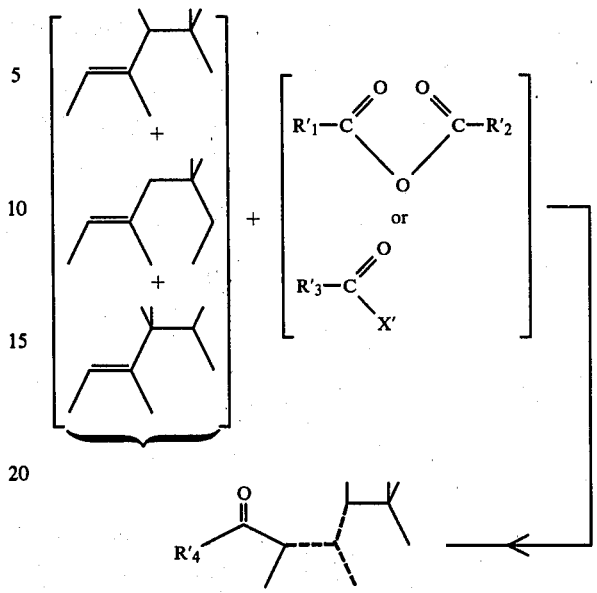

wherein $R_1'$, $R_2'$, and $R_3'$ represents $C_1$–$C_3$ lower alkyl and $R_4'$ is either of $R_1'$, $R_2'$ or $R_3'$ and wherein $X'$ is chloro, or bromo, and the use of the resulting compounds for their organoleptic properties.

The instant application is directed to the use of the compounds defined according to the generic structure:

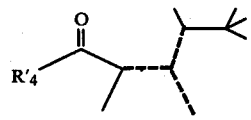

as starting materials wherein $R_4'$ is $C_1$–$C_3$ lower alkyl and wherein one of the dashed lines represents a carbon-carbon double bond and each of the other of the dashed lines represent carbon-carbon single bonds produced according to the process of application for U.S. Letters Patent, Ser. No. 184,132 filed on Sept. 4, 1980 now U.S. Pat. No. 4,321,255 issued on Mar. 23, 1982 entitled "Branched Ketones, Organoleptic Uses Thereof and Process for Preparing Same."

The instant application is also directed to the use of the compounds defined according to the generic structure:

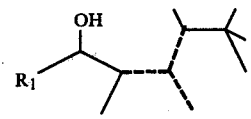

as starting materials wherein $R_1$ is $C_1$–$C_3$ lower alkyl and wherein one of the dashed lines represents a carbon-carbon double bond and each of the other of the dashed lines represent carbon-carbon single bonds produced according to the process of application for U.S. Letters Patent, Ser. No. 252,334 filed on Apr. 9, 1981 entitled "Branched Chain Olefinic Alcohol Sytles Esters and Ethers, Organoleptic Uses Thereof, Processes for Preparing Same and Intermediates Therefore".

THE INVENTION

It has now been determined that certain branched chain secondary alcohols are capable of imparting a variety of flavors and fragrances to various consumable materials. Briefly, my invention contemplates branched chain aliphatic saturated alcohols defined according to the generic structure:

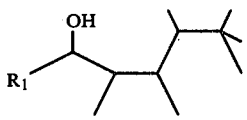

wherein $R_1$ represents $C_1$-$C_3$ alkyl.

The branched chain saturated secondary alcohols of my invention are either usable in admixture with one another or alone, or the isomers are usable in admixture with one another or in admixture with the branched chain olefinic secondary alcohols of application for U.S. Letters Patent, Ser. No. 252,334 filed on Apr. 9, 1981. The isomers of the individual compounds of my invention are stereoisomers for example, two isomers of the identical compound defined according to the structure:

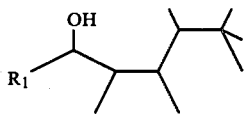

are as follows:

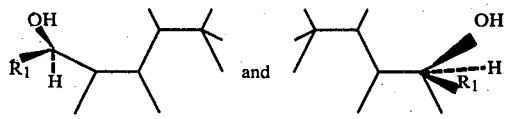

Other stereoisomers exist in view of the fact that the compounds of my invention having the structure:

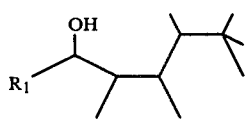

have four asymmetric atoms at the locations marked with an asterisk (*):

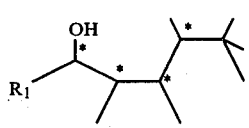

The saturated alcohols of my invention having the structure:

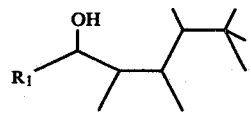

are prepared by means of catalytic hydrogenation or borohydride reduction of the genus of compounds defined according to the structures:

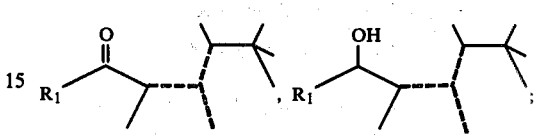

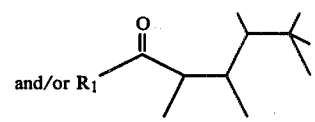

according to the reactions:

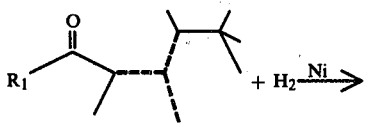

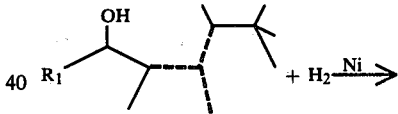

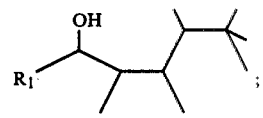

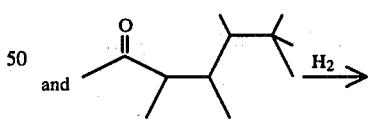

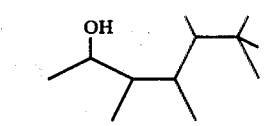

The branched chain olefinic secondary alcohols defined according to the structure:

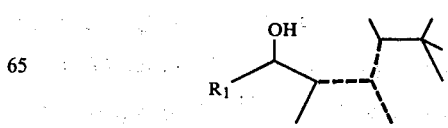

are, in turn, obtained by means of reaction of the ketones having the structure:

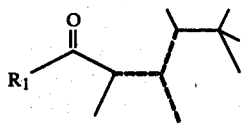

produced according to application for U.S. Letters Patent, Ser. No. 184,132 filed on Sept. 4, 1980 now U.S. Pat. No. 4,321,255 issued on Mar. 10, 1982 entitled "BRANCHED KETONS, ORGANOLEPTIC USES THEREOF AND PROCESSES FOR PREPARING SAME" with a reducing agent such as:
  (a) one or more alkali metal borohydries, e.g., sodium borohydride, lithium borohydride and potassium borohydride;
  (b) hydrogen, using a catalyst such as 5% palladium on carbon, 5% palladium on calcium carbonate or palladium on barium sulfate (e.g., "Lindlar Catalyst"); or
  (c) lithium aluminum hydride;
  (d) aluminum alkoxides, such as aluminum isopropoxide and aluminum secondary propoxide,
according to the reaction:

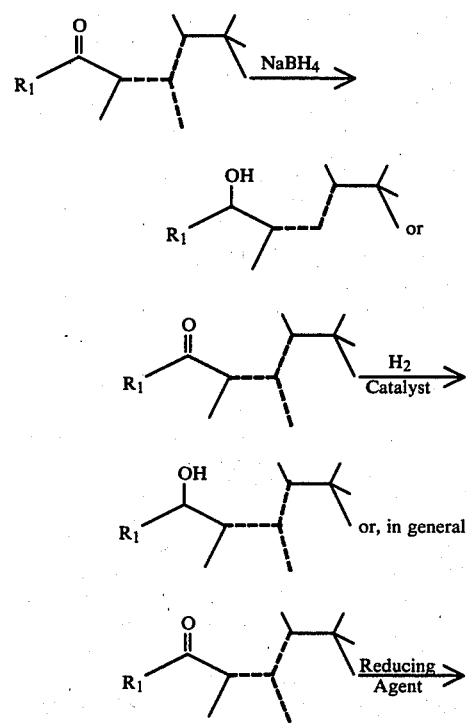

wherein $R_1$ represents $C_1$–$C_3$ alkyl; and wherein the compounds having the dashed lines either represent pure compounds or mixtures wherein one of the dashed lines represents a carbon-carbon double bond (in each of the molecules of the mixture or in each of the compounds) and the other of the dashed lines represent carbon-carbon single bonds.

The compounds defined according to the structure:

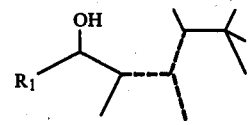

are produced according to application for U.S. Letters Patent, Ser. No. 252,334 filed on Apr. 9, 1981 the disclosure of which is incorporated by reference herein. The instant application is a continuation-in-part of application for U.S. Letters Patent, Ser. No. 252,334 filed on Apr. 9, 1981.

When carrying out the reaction for reacting the ketone having the structure:

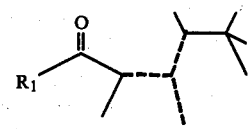

with hydrogen in the presence of a Raney nickel catalyst or a Rhodium catalyst, it is preferably carried out in the absence of a solvent. Thus, a solvent can be used and the workable solvents are ones which "solvate" the carbonal moiety in order to enable the reaction to proceed at a reasonable rate and these are isopropyl alcohol, n-propanol, n-butanol, isobutyl alcohol and t-butyl alcohol.

The temperature of reaction is necessarily a function of:
  (i) the yield desired;
  (ii) the time of reaction;
  (iii) the nature of the solvent used, if any;
  (iv) the pressure of the vapor over the reaction mass;
  (v) the concentration of the reactant having the structure;

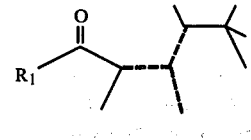

in the solvent.
  (vi) the desired rate of reaction; and
  (vii) the mole ratio of reactant having the structure:

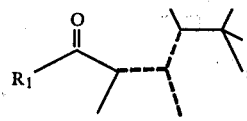

hydrogenation catalyst:total number of moles of hydrogen gas used.

It is preferred to carry out the reaction:

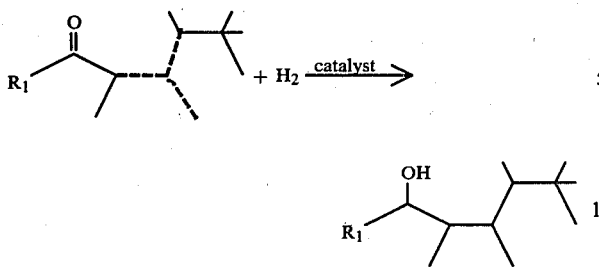

at a temperature in the range of 100°–200° C. and at a pressure in the range of 400–1400 psig.

More strigent conditions are required to carry the reaction:

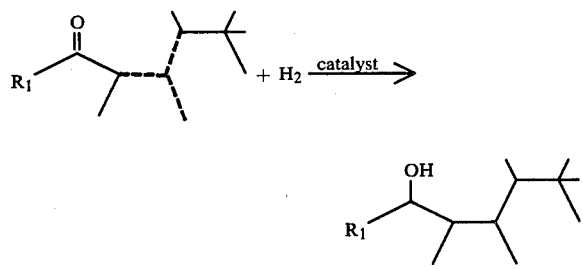

to completion when using a Raney nickel catalyst than when using a Rhodium catalyst. Accordingly, the most preferred catalyst is a supported Rhodium catalyst on carbon.

When it is desired to carry out the hydrogenation reaction on the unsaturated alcohol according to the reaction:

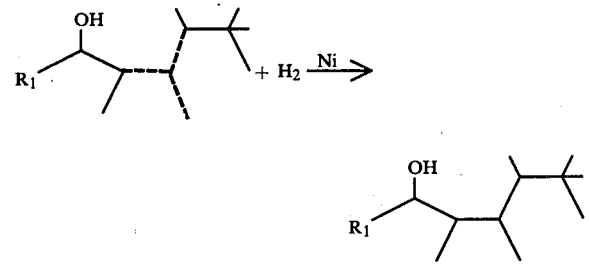

the similar set of conditions as set forth above is required. Thus, the reaction may be carried out using Raney nickel or Rhodium on carbon at a temperature in the range of from about 400° up to 200° C. and a pressure in the range of from about 400 up to 1400 psig.

The compounds having the structure:

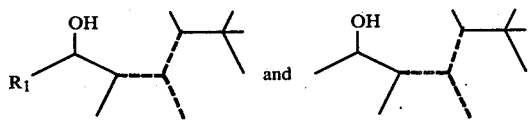

wherein R is $C_1$–$C_3$ alkyl and one of the dashed lines is a carbon-carbon double bond and each of the other of the dashed lines represent carbon-carbon single bonds may be prepared according to the conditions as set forth in application for U.S. Letters Patent, Ser. No. 252,334 filed on Apr. 9, 1981.

The individual branched chain secondary alcohols of my invention can be obtained in purer form or in substantially pure form by a conventional purification techniques. Thus, the products can be purified by distillation, extraction, crystallization, preparative chromatographic techniques (including high pressure liquid chromatography) and the like. It has been found desirable to purify the branched chain saturated secondary alcohols of my invention by fractional distillation under vacuum.

It will be appreciated from the present disclosure that the branched chain saturated secondary alcohols and mixtures thereof according to the present invention can be used to alter, vary, fortify, modify, enhance or otherwise improve the flavor and aroma of a wide variety of materials which are ingested, consumed or otherwise organoleptically sensed, particularly including perfume compositions, perfumed articles and smoking tobacco compositions and smoking tobacco articles.

The term "alter" in its various forms will be understood herein to mean the supplying or imparting of a flavor character or note or aroma character to an otherwise bland, relatively aromaless or tasteless substance, or augmenting an existing flavor or aroma characteristic where the natural flavor or aroma is deficient in some regard or supplementing the existing flavor or aroma impression to modify the orgnoleptic character.

The term "enhance" is intended herein to mean the intensification of a particular aroma or taste nuance (particularly in perfumes, perfumed articles or smoking tobaccos) without the changing of the quality of said nuance and without adding an additional aroma or taste nuance to the consumable material, the organoleptic properties of which are enhanced.

The term "tobacco" will be understood herein to mean a natural product such as, for example, burley, Turkish tobacco, Maryland tobacco, flue-cured tobacco and the like including tobacco-like or tobacco-based products such as reconstituted or homogenized leaf and the like, as well as tobacco substitutes intended to replace natural tobacco, such as lettuce and cabbage leaves and the like. The tobaccos and tobacco products in which the branched chain saturated secondary alcohols of my invention are useful include those designed or used for smoking such as in cigarette, cigar and pipe tobacco, as well as products such as snuff, chewing tobacco and the like.

The branched chain saturated secondary alcohols of my invention can be used to contribute woody (sawdust), mossy, and vetiver aromas with amber undertones. As olfactory agents the branched chain saturated secondary alcohols of this invention can be formulated into or used as components of a "perfume composition."

The term "perfume composition" is used herein to mean a mixture of organic compounds, including, for example, alcohols, other than the alcohols of this invention, aldehydes, ketones, nitriles, esters, and frequently hydrocarbons which are admixed so that the combined odors of the individual components produce a pleasant or desired fragrance. Such perfume compositions usually contain: (a) the main note of the "bouquet" or foundation-stone of the composition; (b) modifiers which round off and accompany the main note; (c) fixatives which include odorous substances which lend a particular note to the perfume throughout all stages of evaporation, and substances which retard evaporation; and (d) topnotes which are usually low-boiling fresh-smelling materials.

In perfume compositions, the individual component will contribute its particular olfactory characteristics but the overall effect of the perfume composition will be the sum of the effect of each ingredient. Thus, the individual compounds of this invention, or mixtures thereof, can be used to alter the aroma characteristics of a perfume composition, for example, by highlighting or moderating the olfactory reaction contributed by another ingredient in the composition.

The amount of branched chain saturated secondary alcohols of this invention which will be effective in perfume compositions depends on may factors, including the other ingredients, their amounts and the effects which are desired. It has been found that perfume compositions containing as little as 0.05% and as much as 5% of the branched chain saturated secondary alcohols of this invention can be used to impart, augment or enhance woody (sawdust), mossy, and vetiver aroma profiles to soaps, cosmetics, solid or liquid anionic, cationic, nonionic and zwitterionic detergents and other products. The amount employed can range up to 50% of the fragrance and can be as low as 1% of the original fragrance and will depend on considerations of cost, nature of the end product, the effect desired in the finished product and the particular fragrance sought.

The branched chain saturated secondary alcohols of this invention can be used alone or in a perfume composition as an olfactory component in detergents, and soaps, space odorants and deodorants, perfumes, colognes, toilet waters, bath salts, hair preparations such as lacquers, brilliantines, pomades, and shampoos, cosmetic preparations such as creams, deodorants, hand lotions and sun screens, powders such as talcs, dusting powders, face powder, and the like. When used as an olfactory component of a perfumed article, as little as 0.05% of one or more of the branched chain saturated secondary alcohols will suffice to impart woody (sawdust), mossy and vetiver aroma nuances with amber-like undertones. Generally no more than 5.0% is required.

In addition, the perfume composition can contain a vehicle or carrier for the branched chain saturated secondary alcohols taken alone or taken together with other ingredients. The vehicle can be a liquid such as an alcohol such as ethanol, a glycol such as propylene glycol, or the like. The carrier can be an absorbent solid such as a gum or a microporous polymer or components for encapsulating the composition such as by means of coacervation.

An additional aspect of our invention provides an organoleptically improved smoking tobacco product and additives therefor, as well as methods of making the same which overcome specific problems heretofore encountered in which specific desired oriental and woody flavor and aroma characteristics are created or enhanced and may be readily controlled and maintained at the desired uniform level regardless of variations in the tobacco components of the blend.

This invention further provides improved tobacco additives and methods whereby various desirable woody and oriental flavor and aroma characteristics may be imparted to smoking tobacco products and may be readily varied and controlled to produce the desired uniform flavoring characteristics prior to and on smoking in the mainstream and in the sidestream.

In carrying out this aspect of our invention, we add to smoking tobacco materials or a suitable substitute therefor (e.g. dried lettuce leaves) and aroma and flavor additive containing as an active ingredient at least one of the secondary alcohols of my invention.

In addition to the one or more secondary alcohols of my invention, other flavoring and aroma additives may be added to the smoking tobacco material or substitute therefor either separately or in admixture with the secondary alcohols as follows:

I. Synthetic Materials

Beta-ethyl-cinnamaldehyde;
Eugenol;
Dipentene;
Alpha-Damascone;
Beta-Damascone;
1-[3-(methylthio)butyryl]2,3,3-trimethyl-cyclohexene;
Beta-Damascenone;
Maltol;
Ethyl maltol;
Delta undecalactone;
Deltadecalactone;
Benzaldehyde;
Amyl acetate;
Ethyl butyrate;
Ethyl acetate;
2-Hexenol-1;
2-Methyl-isopropyl-1,3-nonadiene-8-one;
2,6-Dimethyl-2,6-undecadiene-10-one;
2-Methyl-5-isopropyl acetophenone;
2-Hodroxy-2,5,5,8a-tetramethyl-1-(2-hydroxyethyl)-decahydronaphthalene;
Dodecahydro-3a,6,6,9a-tetramethyl naphtho-(2-1-b)-furan;
4-Hydroxy hexanoic acid, gamma lactone;
Polyisoprenoid hydrocarbons defined in Example V of U.S. Pat. No. 3,589,372, issued on June 29, 1971.

II. Natural Oils

Celery seed oil;
Coffee extract;
Bergamot Oil;
Cocoa extract;
Nutmeg oil; and
Origanum oil.

An aroma and flavoring concentrate containing one or more of the secondary alcohols of my invention and if desired one or more of the above indicated flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste but insofar as the augmentation, or the enhancement or the imparting of the woody and oriental notes are concerned, I have found that satisfactory results are obtained if the proportion by weight of the sum total of secondary alcohols of my invention is between 250 ppm and 1,500 ppm (0.025%–1.5%) of the active ingredients to the smoking tobacco material. I have further found that satisfactory results are obtained if the proportion by weight of the sum total of secondary alcohols used to flavoring material is between 2,500 an 10,000 ppm (0.25%–1.5%).

Any convenient method for incorporating the secondary alcohols in the tobacco product may be employed. Thus, the secondary alcohols taken alone or along with other flavoring additives may be dissolved in a suitable solvent such as ethanol, n-pentene, diethyl ether and/or other volatile organic solvents and the resulting solution may either be sprayed on the cured, cased and blended tobacco material or the tobacco material may be dipped into such solution. Under certain circumstances, a solution of one or more secondary alcohols of this invention taken alone or further together with other flavoring additives as said forth above may be applied by means of a suitable applicator such as a brush or roller on the paper or leaf wrapper for the smoking product, or it may be applied to the filter by either spraying or dipping or coating.

Furthermore, it will be apparent that only a portion of the tobacco or substitute therefor need be treated and the thus treated tobacco may be blended with other tobaccos before the ultimate tobacco product is formed. In such cases, the tobacco treated may have one or more of the secondary alcohols of this invention in excess of the amounts of concentrations above indicated so that when blended with other tobaccos, the final product will have the percentage within the indicated range.

In accordance with one specific example of my invention, and aged, cured and shredded domestic burley tobacco is spread with a 20% ethyl alcohol solution which is a mixture of stereoisomers defined according to the structure:

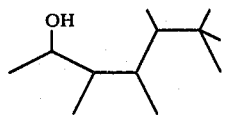

in an amount to provide a tobacco composition containing 800 ppm by weight of the secondary alcohol on a dry basis. Thereafter, the ethyl alcohol is removed by evaporation and the tobacco is manufactured into cigarettes by the usual techniques. The cigarette when treated as indicated has a desired and pleasing aroma which is detectable in the main stream and the side stream when the cigarette is smoked. The aroma is described as being sweet, oriental-like, woody and Turkish tobacco-like.

While our invention is particularly useful in the manufacture of smoking tobacco, such as cigarette tobacco, cigar tobacco and pipe tobacco, other tobacco products formed from sheeted tobacco dust or fines may also be used. Likewise, the secondary alcohols of my invention can be incorporated with materials such as filter tip materials, seam paste, packaging materials and the like which are used along with tobacco to form a product adapted for smoking. Furthermore, the secondary alcohols of this invention can be added to certain tobacco substitutes of natural or synthetic origin (e.g. dried lettuce leaves) and, accordingly, by term "tobacco" as used throughout this specification is meant any composition intended for human consumption by smoking or otherwise, whether compound of tobacco plant parts or substitute materials or both.

The following Examples A–II are given to illustrate techniques for producing the precursors for the compounds defined according to the structure:

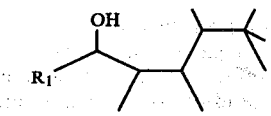

wherein $R_1$ is $C_1$–$C_3$ alkyl. The following Example III is given to illustrate a process for producing compounds defined according to the structure:

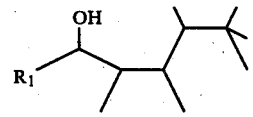

the examples following Example III that is, Examples IV and onward are given to illustrate embodiments of my invention as it is presently preferred to practice it insofar as utilizing the compounds having the structure:

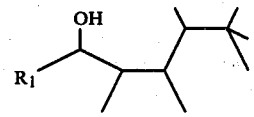

for their organoleptic properties. It will be understood that these examples are illustrative and the invention is not to be considered restricted thereto except as indicated in the appended claims.

EXAMPLE A

Preparation of Di-isoamylene Derivatives

Reaction:

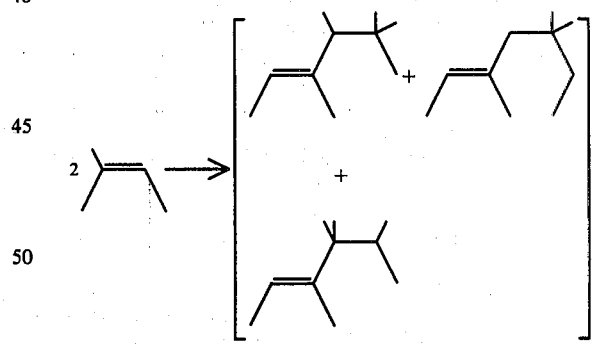

(wherein in each of the molecules indicated, one of the dashed lines is a carbon-carbon double bond and the other of the dashed lines are carbon-carbon single bonds).

Di-isoamylene is prepared according to one of the procedures set forth in the following references:

i—Murphy & Lane, Ind. Eng. Chem., Prod. Res. Dev., Vol. 14, No. 3, 1975 p.167 (Title: Oligomerization of 2-Methyl-2-Butene in Sulfuric and Sulfuric-Phosphoric Acid Mixtures).

ii—Whitmore & Mosher, Vol. 68, J. Am. Chem. Soc., February, 1946, p. 281 (Title: The Depolymerization of 3,4,5,5-Tetramethyl-2-hexene and 3,5,5-Trimethyl-2-heptene in Relation to the Dimerization of Isoamylenes)

The resulting material was distilled in a fractionation column in order to separate the di-isoamylene from the higher molecular weight polymers, which are formed during the reaction as by-products.

FIG. AA represents the GLC profile for the reaction product of Example A using a 70% sulfuric acid catalyst at 35%C.

FIG. AB represents the GLC profile for the reaction product of Example A using an Amberlyst ® 15 acidic ion exchange resin catalyst at a temperature of 150° C.

FIG. AC represents the GLC profile for the reaction product of Example A, using an Amberlyst ® 15 catalyst at 100° C.

FIG. AD represents the GLC profile for the reaction product of Example A, using a sulfuric acid catalyst and an alpha-methylstyrene diluent at 35° C. according to the conditions of United Kingdom patent specification No. 796,130 (crude reaction product).

FIG. AE represents the GLC profile for the reaction product of Example I, using a sulfuric acid catalyst, at 35° C. and an alpha-methyl styrene diluent according to the conditions of United Kingdom patent specification No. 796,130 (distilled reaction product having a boiling range of 36°-38° C. at 4-5 mmHg pressure).

FIG. BA represents th NMR spectrum for Peak 1 of the GLC profile of FIG. AE.

FIG. BB represents the infra-red spectrum for Peak 1 of the GLC profile of FIG. AE.

FIG. CA represents the NMR spectrum for Peak 2 of the GLC profile of FIG. AE.

FIG. CB represents the infra-red spectrum for Peak 2 of the GLC profile of FIG. AE.

FIG. D represents the NMR spectrum for Peak 2 of the GLC profile of FIG. AB.

EXAMPLE I

Preparation of Acetyl Derivative of Diisoamylene

Reaction:

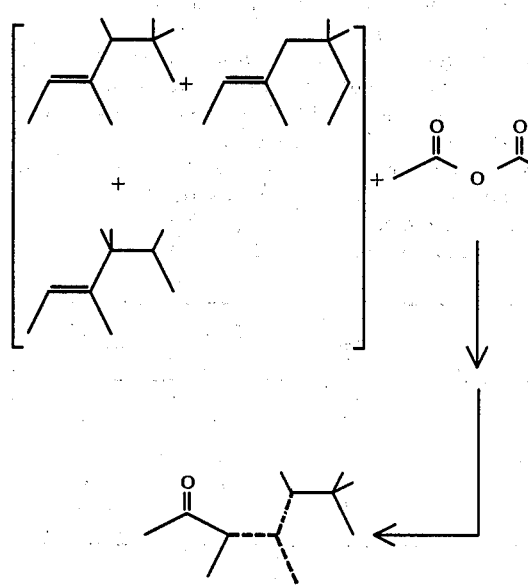

wherein in each of the structures containing dashed lines, these structures represent mixtures molecules wherein in each of the molecules, one of the dashed lines represents a carbon-carbon double bond and each of the other of the dashed lines respresent carbon-carbon single bonds.

Into a 2-liter reaction flask equipped with stirrer, thermometer, reflex condenser and heating mantle, is placed 1000 g of acetic anydride and 80 g of boron trifluoride diethyl etherate. The resulting mixture is heated to 80° C. and, over a period of 40 minutes, 690 g of diisoamylene prepared according to the illustration in Example A, supra is added. The reaction mass is maintained at 82°-85° C. for a period of 5.5 hours, whereupon it is cooled to room temperature. The reaction mass is then added to one liter of water and the resulting mixture is stirred thereby yielding two phases; an organic phase and an aqueous phase. The organic phase is separated from the aqueous phase and neutralized with two liters of 12.5% sodium hydroxide followed by one liter of saturated sodium chloride solution. The resulting organic phase is then dried over anhydrous sodium sulfate and distilled in a one plate distillation column, yielding the following fractions:

| Fraction No. | Vapor Temp. (°C.) | Liquid Temp. (°C.) | mm/Hg Pressure | Weight of Fraction (g.) |
|---|---|---|---|---|
| 1 | 33/68 | 62/77 | 8/8 | 161 |
| 2 | 69 | 79 | 4 | 100 |
| 3 | 72 | 86 | 3.0 | 191 |
| 4 | 88 | 134 | 3.0 | 189 |

The resulting material is then distilled on a multi-plate fractionation column, yielding the following fractions at the following reflux ratios:

| Fraction No. | Vapor Temp. (°C.) | Liquid Temp. (°C.) | mm/Hg Pressure | Reflux Ratio R/D | Weight of Fraction (g.) |
|---|---|---|---|---|---|
| 1 | 30/65 | 62/83 | 5/5 | 9:1 | 30.8 |
| 2 | 68 | 84 | 5 | 9:1 | 52.8 |
| 3 | 68 | 85 | 5 | 9:1 | 34 |
| 4 | 69 | 87 | 5 | 9:1 | 43 |
| 5 | 69 | 87 | 5 | 9:1 | 34 |
| 6 | 71 | 88 | 4 | 4:1 | 41 |
| 7 | 70 | 88 | 5 | 4:1 | 36.5 |
| 8 | 71 | 91 | 5 | 4:1 | 42 |
| 9 | 73 | 95 | 3 | 4:1 | 42.5 |
| 10 | 80 | 106 | 3 | 4:1 | 39 |
| 11 | 80 | 142 | 3 | 4:1 | 50.8 |
| 12 | 80 | 220 | 3 | 4:1 | 24 |

Frations 2-9 are bulked and GLC, NMR, IR and mass spectral analyses yield the information that the resulting material is a mixture of cis and trans isomers having a generic structure:

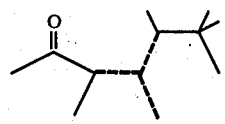

wherein in each of the molecules, one of the dashed lines is a carbon-carbon double bond and the other of the dashed lines is a carbon-carbon single bond and, primarily, this mixture contains the molecular species (cis and trans isomers) as follows:

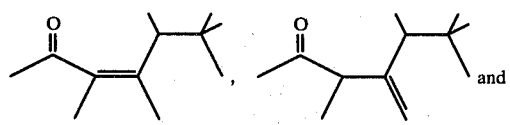

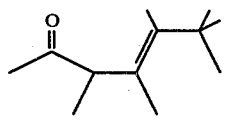

FIG. 1 sets forth the GLC profile for the reaction product of Example I, containing compounds defined according to the structure:

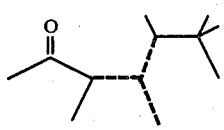

wherein in each molecule of the mixture, one of the dashed lines is a carbon-carbon double bond and the other of the dashed lines are carbon-carbon single bonds.

FIG. 2A represents the infra-red spectrum of Peak 3 of the GLC profile of FIG. 1.

FIG. 2B represents the infra-red spectrum of Peak 4 of the GLC profile of FIG. 1.

FIG. 2C represents the infra-red spectrum for Peak 5 of the GLC profile of FIG. 1.

FIG. 2D represents the infra-red spectrum for Peak 7 of the GLC profile of FIG. 1.

FIG. 2E represents the infra-red spectrum for Peak 7 of the GLC profile of FIG. 1.

FIG. 2F represents the infra-red spectrum for Peak 8 of the GLC profile of FIG. 1.

FIG. 2G represents the infra-red spectrum for Peak 9 of the GLC profile of FIG. 1. produced according to Example I.

FIG. 2K represents the NMR spectrum for the compound having the structure:

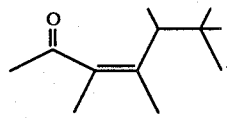

produced according to Example I.

FIG. 2L represents the NMR spectrum for the compound containing the structure:

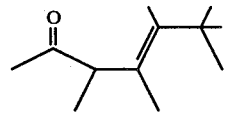

produced according to Example I.

EXAMPLE II

Preparation of Isobutyryl Derivative of Diisoamylene

Reaction:

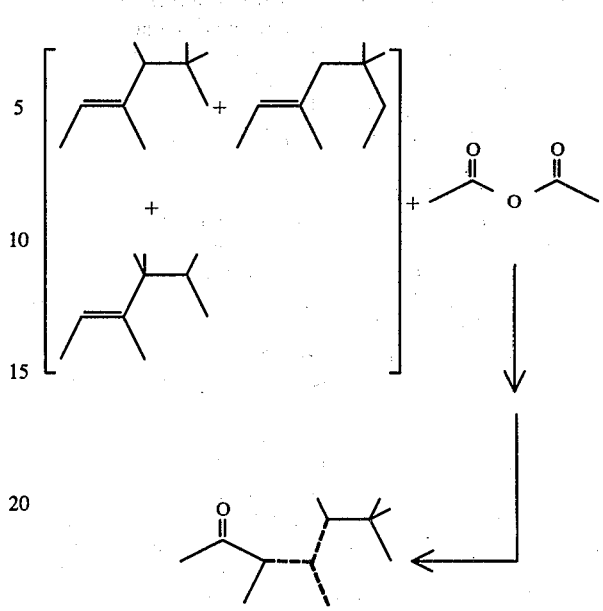

(wherein in each of the structures containing the dashed lines, these structures represent mixtures of molecules wherein in each of the molecules, one of the dashed lines represents a carbon-carbon double bond and each of the other of the dashed lines represent carbon-carbon single bonds).

Into a 12-liter reaction flask, equipped with nitrogen blanket apparatus, gas addition set up and dry tap and sodium hydroxide scrubber on reaction outlet is placed 2358 g (23.1 moles) of acetic anhydride and 4620 g (33 moles) of diisoamylene prepared according to Example AE. The resulting mixture is heated to 55° C. while maintaining the reaction mass at 54°–55° C. over a period of 1 hour, 169 g (2.5 moles) of boron trifluoride gas is added to the reaction mass with stirring.

The reaction mass is then heated for a period of 2 hours with stirring at 55% °C.

The reaction mass is then transferred to a separatory funnel and in the separatory funnel the reaction mass is washed with 4 liters of 12.5% aqueous sodium hydroxide. The aqueous layer is separated from the organic layer and the organic layer is washed with three 6 liter volumes of water until the pH is about 7.

The reaction mass is then distilled on a two inch splash column yielding the following fractions:

| Fraction No. | Vapor Temp. (°C.) | Liquid Temp. (°C.) | Vacuum mm.Hg. Pressure |
|---|---|---|---|
| 1 | 28/47 | /56 | 50/8 |
| 2 | 63 | 80 | 4.0 |
| 3 | 76 | 87 | 4.0 |
| 4 | 87 | 96 | 3.5 |
| 5 | 87 | 100 | 3.5 |
| 6 | 90 | 113 | 3.5 |
| 7 | — | — | 3.5 |

Fraction 4–7 are then bulked for subsequent reaction in Example III.

FIG. 3 is the GLC profile for the current reaction product (Conditions: 6'×¼ inch 12% S.F. 96, column programmed at 100°–220° C. at 8° C. per minute).

FIG. 4 is the GLC profile for bulked fractions 4–7 of the foregoing distillation (Conditions: 6'×¼ inch 12% S.F. 96, column programmed at 100°–220° C. at 8° C. per minute).

EXAMPLE III

Preparation of 3,4,5,6,6-Pentamethyl-Hexanol-2
Reaction:

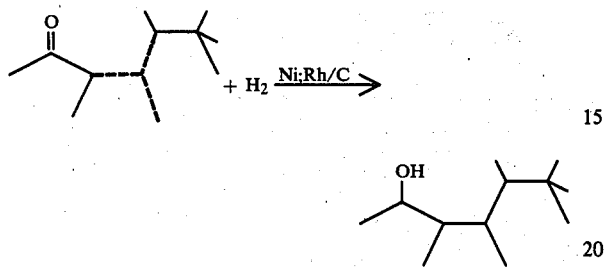

Into a 1 liter autoclave equipped for 2000 psig pressure is placed 498 g of the reaction product of Example II (bulked fractions 4–7) and 16 g of Raney nickel. The autoclave is sealed and the products are hydrogenated at a temperature in the range of 460–480 psig and a temperature in the range of 130°–150° C. for a period of 15 hours. The autoclave is then cooled down, depressurized and opened and the Raney nickel catalyst is filtered and replaced with 2.5 g of 5% Rhodium on carbon catalyst. The autoclave is then sealed and pressurized at a pressure of 460–610 psig at a temperature in the range of 125°–150° C. for a period of 15 hours. The autoclave is then cooled down and opened and the reaction mass is filtered. The reaction mass is then distilled on a 14 inch Figrux column yielding the following fractions:

| Fraction No. | Vapor Temp. (°C.) | Liquid Temp. (°C.) | Vacuum mm.Hg. Pressure | Weight of Fraction |
|---|---|---|---|---|
| 1 | 58/ | 78/ | 1.3 | 5.0 |
| 2 | 80 | 97 | 3.0 | 3.9 |
| 3 | 81 | 98 | 2.8 | 7.0 |
| 4 | 81 | 99 | 2.8 | 6.8 |
| 5 | 82 | 100 | 2.8 | 14.1 |
| 6 | 83 | 103 | 2.8 | 13.1 |
| 7 | 84 | 105 | 2.8 | 15.1 |
| 8 | 89 | 109 | 2.8 | 14.7 |
| 9 | 103 | 112 | 2.8 | 14.3 |
| 10 | 104 | 109 | 2.0 | 19.9 |
| 11 | 105 | 110 | 2.0 | 20.0 |
| 12 | 105 | 110 | 2.0 | 47.9 |
| 13 | 105 | 110 | 2.0 | 49.1 |
| 14 | 106 | 111 | 2.0 | 47.6 |
| 15 | 107 | 112 | 2.0 | 41.0 |
| 16 | 108 | 113 | 2.0 | 23.3 |
| 17 | 109 | 114 | 2.0 | 24.0 |
| 18 | 110 | 130 | 2.0 | 19.8 |
| 19 | 100 | 200 | 2.0 | 10.4 |
| 20 | 90 | 230 | 2.0 | 4.9 |

Fractions 12–15 are bulked for subsequent organoleptic utilization.

FIG. 5 is the GLC profile for bulked fractions 12–15 of the foregoing distillation (conditions: 10'×¼ inch, 10% carbowax column programmed at 80°–225° C. at 8° C. per minute).

FIG. 6 is the infra-red spectrum for bulked fractions 12–15.

FIG. 7 is the NMR spectrum for bulked fractions 12–15 of the foregoing distillation (solvent: CFCl$_3$; field strength 100 MHz).

EXAMPLE IV

Perfume Formulation

The following vetiver perfume formulation is prepared:

| Ingredients | Parts by Weight |
|---|---|
| Vetivone | 25.0 |
| Compound having the structure: | |
| 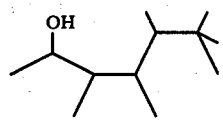 | |
| Produced according to Example III, bulked fractions 12–15 | 25.0 |
| Vetiverol | 5.0 |
| Musk Ketone | 8.0 |
| Styrax essence | 12.5 |

The addition of the compound having the structure:

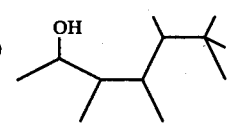

prepared according to Example III impart to this vetiver formulation a woody, mossy, amber undertone.

EXAMPLE V

Perfumed Liquid Detergent

Concentrated liquid detergents with aromas as described in Table I below (which detergents are produced from the lysine salt of n-dodecyl benzene sulfonic acid as more specifically described in U.S. Pat. No. 3,948,818 issued on Apr. 6, 1976) are prepared containing one of the substances set forth in Table I below. They are prepared by adding and homogeneously mixing the appropriate quantity of substance as indicated in Table I below. The detergents all possess aroma profiles as set forth in Table I below, the intensity increasing with greater concentrations of the composition of matter as set forth in Table I below:

TABLE I

| Aroma Ingredient | Aroma Profile |
|---|---|
| Secondary alcohol produced according to Example III having the structure:<br>(bulked fractions 12–15). | A woody (sawdust), mossy, vetiver aroma, amber undertones. |
| Perfume composition of Example IV. | A vetiver aroma with woody (sawdust), mossy and amber undertones. |

EXAMPLE VI

Preparation of a Cologne and Handkerchief Perfume

Aroma imparting and augmenting ingredients as defined according to Table I in Example V are incorporated into colognes at concentrations of 1.5%, 2.0%, 2.5%, 3.0%, 4.0% and 5.0% in 75%, 80, 80%, 90% and 95% solutions of aqueous ethanol; and into handkerchief perfumes at concentrations of 15%, 20%, 25% and 30% (in 80%, 85% and 95% aqueous ethanol solutions). The use of the compositions of matter as set forth in Table I of Example V affords distinct and definitive aroma profiles as set forth in Table I of Example V to the handkerchief perfumes and to the colognes.

EXAMPLE VII

Preparation of a Soap Composition

One hundred grams of soap chips (IVORY ®) manufactured by the Procter & Gamble Company of Cincinnati, Ohio, are melted and intimately admixed with one of the aroma materials as set forth in Table I of Example V, supra, the amount of composition of matter of Table I of Example V being one gram of each composition of matter. The conditions of mixing are: 180° C., 3 hours, 12 atmospheres pressure. At the end of the mixing cycle, while the soap is still under 12 atmospheres pressure, the mixture of soap and perfume ingredient is cooled to room temperature. At this temperature, the resulting mixture is in a solid state. The resulting soap block is then cut up into soap cakes. Each of the soap cakes manifests an excellent aroma as set forth in Table I of Example V. None of the soap samples show any discoloration even after two weeks in the oven at 90° F.

EXAMPLE VIII

Preparation of a Detergent Composition

A total of 100 grams of a detergent powder (nonionic detergent powder containing a proteolytic enzyme prepared according to Example I of Canadian Pat. No. 985,190 issued on Mar. 9, 1976) is mixed with 0.15 grams of one of the compositions of matter as set forth in Table I of Example V until a substantially homogeneous composition is obtained. Each of the compositions has excellent aroma profiles as set forth in Table I of Example V.

EXAMPLE IX

Perfumed Liquid Detergents

Concentrated liquid detergents with rich, pleasant aromas as set forth in Table I of Example V are prepared containing 0.10%, 0.15% and 0.20% of each of the compositions of matter set forth in Table I of Example V. They are prepared by adding and homogeneously admixing the appropriate quantity of composition of matter of Table I of Example V in the liquid detergent. The liquid detergents are all produced using anionic detergents containing a 50:50 mixture of sodium lauroyl sarcosinate and potassium N-methyl lauroyl tauride. The detergents all possess pleasant aromas as defined in Table I of Example V, the intensity increasing with greater concentrations of composition of matter of Table I of Example V.

EXAMPLE X

Tobacco Formulation

A tobacco mixture is prepared by admixing the following ingredients:

| Ingredients | Parts by Weight |
|---|---|
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco. The following flavor formulation is prepared:

| Ingredients | Parts by Weight |
|---|---|
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above stated tobacco flavor formulation is applied at the rate of 1.0% to all of the cigarettes produced using the above tobacco formulation. One-half of the cigarettes are then treated with 500–1000 ppm or 1000 ppm of the secondary alcohol mixture defined according to the structure:

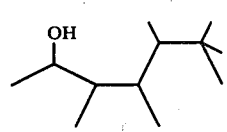

produced according to Example III (bulked fractions 12–15).

The second half of the cigarettes are "control cigarettes" and do not contain any of the alcohol produced in Example III but only contain untreated flavor formulation as set forth above. The control cigarettes and the treated experimental cigarettes are then evaluated by paired comparison and the results are as follows:

The experimental cigarettes are found to have more body and to be, on smoking, more Turkish tobacco-like, more aromatic and to have spicy and woody/oriental aroma and taste nuances in both the main stream and the side stream. These aroma nuances are missing from the control cigarettes. Prior to smoking, the experimental cigarettes have dry, woody, vetiver-like, musty and earthy nuances.

What is claimed is:

1. At least one compound defined according to the structure:

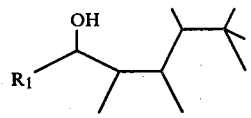

wherein $R_1$ is $C_1$–$C_3$ alkyl.

2. The compound of claim 1 wherein $R_1$ is methyl.

3. A composition of matter including a major proportion of a compound having the structure:

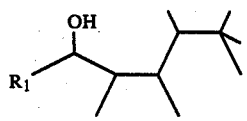

wherein $R_1$ is $C_1$–$C_3$ alkyl produced according to the process consisting essentially of the step of treating with hydrogen in the presence of a catalyst selected from the group consisting of Raney nickel and Rhodium at least one compound defined according to the structure:

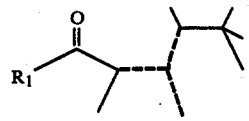

wherein in the compound having the structure:

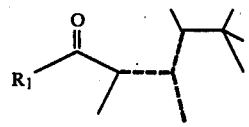

one of the dashed lines is a carbon-carbon double bond and each of the other of the dashed lines are carbon-carbon single bonds and the temperature in the range of from 100° C. up to 200° C. and at a pressure in the range of from 400 psig up to 1400 psig.

4. The product consisting essentially of a compound having the structure:

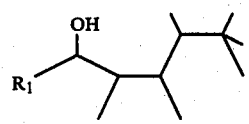

produced according to the process consisting essentially of the step of reacting with hydrogen in the presence of a catalyst selected from the group consisting of Raney nickel and Rhodium at least one compound defined according to the structure:

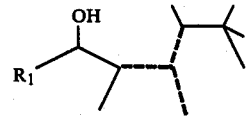

wherein $R_1$ is $C_1$–$C_3$ alkyl and in the structure:

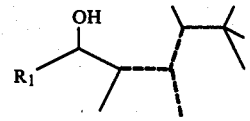

one of the dashed lines is a carbon-carbon double bond and each of the other of the dashed lines are carbon-carbon single bonds.

5. The product of claim 3 wherein $R_1$ is methyl.
6. The product of claim 4 wherein $R_1$ is methyl.

* * * * *